US005763167A

United States Patent [19]
Conrad

[11] Patent Number: 5,763,167
[45] Date of Patent: Jun. 9, 1998

[54] APPLICATIONS OF FLUORESCENT N-NUCLEOSIDES AND FLUORESCENT STRUCTURAL ANALOGS OF N-NUCLEOSIDES

[75] Inventor: Michael J. Conrad, San Diego, Calif.

[73] Assignee: Chromagen, San Diego, Calif.

[21] Appl. No.: 214,994

[22] Filed: Mar. 21, 1994

Related U.S. Application Data

[63] Continuation of Ser. No. 834,456, Feb. 12, 1992, abandoned.
[51] Int. Cl.$^6$ ..................................................... C12Q 1/68
[52] U.S. Cl. ........................... 435/6; 536/24.3; 536/26.13; 536/28.4
[58] Field of Search ..................... 435/6; 536/24.3, 536/26.13, 28.4

[56] References Cited

U.S. PATENT DOCUMENTS

| | | | |
|---|---|---|---|
| 3,960,840 | 6/1976 | Secrist, III et al. | 536/26.6 |
| 4,415,732 | 11/1983 | Caruthers et al. | 536/26.5 |
| 4,683,202 | 7/1987 | Mullis | 435/91 |
| 4,828,979 | 5/1989 | Klevan et al. | 435/6 |
| 4,849,513 | 7/1989 | Smith et al. | 536/27 |
| 4,910,300 | 3/1990 | Urdea et al. | 536/287 |
| 4,965,350 | 10/1990 | Inoue et al. | 536/22.1 |
| 5,091,310 | 2/1992 | Innis | 435/91 |
| 5,093,232 | 3/1992 | Urdea et al. | 435/6 |

FOREIGN PATENT DOCUMENTS

| | | |
|---|---|---|
| 0235301 | 9/1987 | European Pat. Off. |
| 9316094 | 2/1992 | WIPO |

OTHER PUBLICATIONS

Urdea, Mickey S., Janice Kolberg, Jennifer Clyne, Joyce A. Running, Diana Besemer, Brian Warner, and Ray Sanchez-Pescador (1989) "Application of a Rapid Non-Radioisotopic Nucleic Acid Analysis System to the Detection of Sexually Transmitted Disease-Causing Organisms and Their Assoicated Antimicrobial Resistance" Clin. Chem. 35(8):1571–1575.

Weeks, Ian, Iraj Beheshti, Frank McCapra, Anthony K. Campbell, and J. Stuart Woodhead (1983) "Acridinium Esters as High-Specific-Activity Labels in Innumoassay" Clin. Chem. 28(8):1474–1479.

Hori Makoto, Etsuko Ito, Tomohisa Takita, Gunji Koyama, Tomio Takeuchi, and Hamao Umezawa (1964) "A New Antibiotic, Formycin" The Journal of Antibiotics, Ser. A 17(3):96–99

Aizawa, Shojiro, Tetsuro Hidaka, Noboru Otake, Hiroshi Yonehara, Kyoshi Isono, Noriko Igarashi, Saburo Suzuki (1965) "Studies on a New Antibiotic, Laurusin" Agr. Biol. Chem. 29(4):375–376.

Koyama, Gunji, Kenji Maeda, and Hamao Umezawa (1966) "The Structural Studies of Formycin and Formycin B" Tetrahedron Letters 6:597–402.

Uematsu, Takayoshi, and R. J. Suhadolnik (1972) "Pseudouridine, Isolation and Biosythesis of the Nucleoside Isolated from the Culture Filtrates of *Streptoverticillium ladakanus*" Biochemistry 11(25):4669–4674.

Ochi, Kozo, Seiichi Iwamoto, Eiji Hayase, Shigetaka Yashima, and Yoshiro Okami (1974) "Biosynthesis of Formycin, Role of Certain Amino Acids in Formycin Biosythesis" The Journal of Antibiotics 27(12):909–916.

Ward, D.C., A. Cerami, and E. Reich (1969) "Biochemical Studies of the Nucleoside Analogue, Formycin" The Journal of Biological Chemistry 244(12):3243–3250.

Ward, D.C., and E. Reich (1969) "Fluorescence Studies of Nucleosides and Polynucleotides" The Journal of Biological Chemistry 244(5):1228–1237.

Ward, D.C., and E. Reich (1968) "Conformational Properties of Polyformycin: A Polyribonucleotide with Individual Residues in the Syn Conformation" Biochemistry 61:1494–1501.

Udenfriend, Sidney, and Perola Zaltzman (1962) "Fluorescence Characteristics of Purines, Pyrimidines, and Their Derivatives: Measurement of Guanine in Nucleic Acid Hydrolyzates" 3:49–59.

Reisfeld, Avi, Jeffrey M. Rothenberg, Edward A. Bayer, and Meir Wilchek (1987) "Nonradioactive Hybridization Proves Prepared by the Reaction of Biotin Hydrazide with DNA" 142(2):519–526.

Bayer, Edward A, Mariano G. Zalis, and Meir Wilchek (1985) "3-(N-Maleimido-propionyl) Biocytin: A Versatile Thiol-Specific Biotinylating Reagent" Analytical Biochemistry 149:529–536.

Langer, Pennina R., Alex A. Waldrop, and David C. Ward (1981) "Enzymatic synthesis of biotin-labeled polynucleotides: Novel nucleic acid affinity probes" 78(11):6633–6637.

Saiki, Randall K., Stephen Scharf, Fred Faloona, Kary B. Mullis, Glenn T. Horn, Henry A. Erlich, and Norman Arnheim (1985) "Enzymatic Amplification of β–Globin Genomic Sequences and Restriction Site Analysis for Diagnosis of Sickle Cell Anemia" Science vol. 230 1350–1354.

(List continued on next page.)

*Primary Examiner*—Scott W. Houtteman
*Attorney, Agent, or Firm*—Saliwanchik, Lloyd & Saliwanchik

[57] ABSTRACT

Structural analogs of the six non-fluorescent N-nucleosides commonly found in RNA and DNA, which are inherently fluorescent under physiological conditions, are identified and methods for their preparation provided. Such analogs may be incorporated into DNA and/or RNA oligonucleotides via either enzymatic or chemical synthesis to produce fluorescent oligonucleotides having prescribed sequences. Such analogous sequences may be identical to, or the analogous complement of, template or target DNA or RNA sequences to which the fluorescent oligonucleotides can be hybridized. Methods of preparing either RNA or DNA oligonucleotide probes of the invention, intermediates used in such methods, and methods of using the probes of the invention in oligonucleotide amplification, detection, identification, and/or hybridization assays are also provided.

7 Claims, 13 Drawing Sheets

OTHER PUBLICATIONS

Bobo, Unda, Francois Coutlee, Robert H. Yoken, Thomas Quinn, and Raphael P. Viscidi (1990) "Diagnosis of *Chlamydia trachomatis* Cervical Infection by Detection of Amplified DNA with an Enzyme Immunoassay" Journal of Clinical Microbiology 28(9):1968–1973.

Viscidi, Raphael P., Carla J. Connelly, and Robert H. Yolken (1986) "Novel Chemical Method for the preparation of Nucleic Acids for Nonisotopic Hybridization" Journal of Clinical Microbiology 23(2):311–317.

Draper, David E., and Larry Gold (1980) "A Method for Linking Fluorescent Labels to Polynucleotides: Application to Studies of Ribosome–Ribonucleic Acid Internations" Biochemistry 19:1774–1781.

Keller, George, H., Cecilia U. Cumming, Dao–Pei Huang, Mark M. Manak, and Robert Ting (1988) "A Chemical Method for Introducing Haptens onto DNA Probes" Analytical Biochemistry 170:441–450.

Ruth, Jerry L., Carol Morgan, and April PPasko (1985) "Linker Arm Nucleotide Analogs Useful in Oligonucleotide Synthesis" 4:93 (abstract).

Jablonski, Edward, Ellen W. Moomaw, Richard H. Tullis, and Jerry L. Ruth (1986) "Preparation of oligodeoxynucleotide–alkaline phosphatase conjugates and their use as hybridization probes" Nucleic Acids Research 14(15):6115–6128.

Forster, Anthony C., James L. McInnes, Derek C. Skingle, and Robert H. Symons (1986) "Non–radioactive hybridization probes prepared by the chemical labelling of DNA and RNA with a novel reagent, photobiotin" Nucleic Acids Research 13(3):745–761.

Bayer, Edward A., and Meir Wilchek (1980) "The Use of the Avidin–Biotin Complex as a Tool in Molecular Biology" Methods of Chemical Analysis, Joh Wiley & Sons, New York, David Glick [ed.], vol. 26 pp.1–45.

Lee, William T., and Daniel H. Conrad (1984) "The Murine Lymphocyte Receptor for IgE" J. Exp. Med. 159:1790–1795.

Cardullo, Richard A., Sudhir Agrawal, Carlos Flores, Paul C. Zamecnik, and David E. Wolf (1988) "Detection of nucleic acid hybridization by nonradiative fluorescence resonance energy transfer" Proc. Natl. Acad. Sci. USA 85:8790–8794.

Brumbaugh, John A., Lyle R. Middendorf, Daniel L. Grone, and J.L Ruth (1988) "Continuous, on–line DNA sequencing using oligodeoxynucletide primers with multiple fluorophores" Proc. Natl. Acad. Sci. USA 85:5610–5616.

Sproat, Brian S., Agus I. Lamond, Barbro Beijer, Philippe Neuner, and Ursula Ryder (1989) "Highly efficient chemical sythesis of 2'–O–methyloligoribonucleotides and tetrabiotinylated derivatives; novel probes that are resistant to degradation by RNA or DNA specific nucleases" Nucleic Acids Research 17(9):3373–3386.

Urdea, Mickey S., Brian D. Warner, Joyce A. Running, Michelle Stempien, Jennifer Clyne, and Thomas Horn (1988) "A comparison of non–radioisotopic hybridization assay methods using fluorescent, chemiluminiscent and enzyme labeled sythetic oligodeoxyribonucleotide probes" Nuceic Acids Research 16(11):4937–4956.

Allen, Dwayne J., Paul L. Darke, and Stephen J. Benkovic (1989) "Fluorescent Oligonucleotides and Deozynucleotide Triphosphates: Preparation and Their Interaction with the Large (Klenow) Fragment of *Escherichia coli* DNA Polymerase I" Biochemistry 28:4601–4607.

Haralambidis, Jim, Lucy Duncan, Karin Angus, and Geoffrey W. Tregear (1990) "The Syntehsis of polyamide—oligonucleotide conjugate molecules" Nucleic Acids Research 18(3):493–499.

Agrawal, Sudhir, and Paul C. Zamecnik (1990) "Site specific functionalization of oligonucleotides for attaching two different reporter groups" Nucleic Acids Research 18(18):5419–5423.

Robins, M.J., J.S. Wilson (1981) "Smooth and Efficient Deoxygenation of Secondary Alcohols. A General Procedure for the Conversion of Ribonucleosides to 2'–Deoxynucleosides" J. Am. Chem. Soc. 103:932–933.

Hideo, L et al. (1988) "Fluorescent Nucleoside or Nucleotide" Patent Abstracts of Japan, vol. 12, No. 139, abstract No. JP62255499.

Hideo, L et al. (1987) "Fluorescent Nucleoside or Nucleotide" Patent Abstracts of Japan, vol. 11, No. 259, abstract No. JP62059293.

Secrist III, John A. et al. (1972) "Fluorescent Modification of Adenosine–Containing Coenzymes, Biological Activities and Spectroscopic Properties" Biochemistry 11(19):3499–3506.

Sarfati, S.R. et al. (1987) "Synthesis of Fluorescent or Biotinylated Nucleoside Compounds" Tetrahedron 43(15):3491–3496.

Kulikowska,Ewa et al.(1986) "Properties of two unusual, and fluorescent, substrates of purine–nucleoside phosphorylase:7–methylguanosine and 7–methylinosine" Bio.et Bio.Acta874:355–363.

Schram, K.H., L.B. Townsend (1974) "Fluorescent Nucleoside Derivatives of Imidazo (1,2–C) Pyrrolo(2,3–d)Pyrimidine A New and Novel Heterocyclic Ring System" Tet.Letters 14:1345–1348.

Cocuzza, Anthony J. (1988) "Total Synthesis of 7–IODO–2', 3'–Dideoxy–7–Deazapurin Nucleosides, Key Intermediates in the Preparation of Reagents for the Automated Sequencing of DNA" Tetrahedron Letters 29(33):4061–4064.

Darlix, Biochem. 10:1525–31, (1971).

Ward et al. J. Biochem. 224(5):1228–37, Mar. 10, 1969.

Adenosine

Guanosine or Inosine

Cytidine

Thymidine or Uridine

FORMYCIN A

FORMYCIN B

OXYFORMYCIN B

TOYOCAMYCIN

SANGIVAMYCIN

PSEUDOURIDINE

SHOWDOMYCIN

PYRAZOMYCIN

MINIMYCIN (ONLY THE PURINE ANALOGS ARE ILLUSTRATED BELOW)

1, N6 ETHENO
PURINE NUCLEOTIDES

1, N6 ETHENO
PYRIMIDINE NUCLEOTIDES

2'-O-(1)-NAPHTHOYL
Adenosine

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Chlamydia trachomatis
        ( C ) INDIVIDUAL ISOLATE: L2/434/Bu
        ( G ) CELL TYPE: Bacterium ( v i i ) IMMEDIATE SOURCE:
        ( A ) LIBRARY: lambda 1059 recombinant
        ( B ) CLONE: lamdba gt11/L2/33

( v i i i ) POSITION IN GENOME:
        ( A ) CHROMOSOME/SEGMENT: omp1l2 ORF ( x i ) SEQUENCE DESCRIPTION: SEQ ID NO:1:

```
AACGTTCGAG ACGGACACCC CTTAGGACGA CTTGGTTCG                                    39
```

( 2 ) INFORMATION FOR SEQ ID NO:2:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: transcribed DNA or RNA ( i i i ) HYPOTHETICAL: NO ( i v ) ANTI-SENSE: YES ( i x ) FEATURE:
        ( A ) NAME/KEY: Complementary probe
        ( C ) IDENTIFICATION METHOD: Hybridization to SEQ ID NO. 1
        ( D ) OTHER INFORMATION: Control for SEQ ID NO. 3

( x i ) SEQUENCE DESCRIPTION: SEQ ID NO:2:

```
TTGCAAGCTC TGCCTGTGGG GAATCCTGCT GAACCAAGC                                    39
```

( 2 ) INFORMATION FOR SEQ ID NO:3:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: transcribed DNA or RNA ( i i i ) HYPOTHETICAL: NO ( i v ) ANTI-SENSE: YES ( i x ) FEATURE:
        ( A ) NAME/KEY: Analogous complementary probe
        ( C ) IDENTIFICATION METHOD: Hybridization to SEQ ID NO. 1

( D ) OTHER INFORMATION: Analog to SEQ ID NO. 2

( x i ) SEQUENCE DESCRIPTION: SEQ ID NO:3:

```
TTGCNNGCTC TGCCTGTGGG GNNTCCTGCT GNNCCNNGC                     3 9
```

APPLICATIONS OF FLUORESCENT N-NUCLEOSIDES AND FLUORESCENT STRUCTURAL ANALOGS OF N-NUCLEOSIDES

This application is a continuation of application Ser. No. 07/834,456, filed Feb. 12, 1992 now abandoned.

BACKGROUND OF THE INVENTION

A. Field of the Invention

The present invention relates to fluorescent structural analogs of the non-fluorescent nucleosides commonly found in DNA and RNA, methods of their derivatization and subsequent use in the synthesis of fluorescent oligonucleotides, and to their new and useful applications both as fluorescent monomers and in fluorescent oligonucleotides having prescribed sequences. Additionally, it relates to applications in which fluorescent structural analogs are substituted for specific non-fluorescent nucleosides in prescribed DNA or RNA sequences and to methods of using fluorescent oligonucleotides as hybridization reagents and probes for diagnostic and therapeutic purposes.

B. General Description of the Art

The six commonly occurring N-nucleosides which predominate in the composition of DNA and RNA from all sources have the structures shown in FIG. 1 wherein $R_6$ is H for inosine and $NH_2$ for guanosine, Rg is H for uridine and $CH_3$ for thymidine. Furthermore, $R_{12}$, $R_{14}$=OH for ribonucleotides, $R_{12}$=OH, $R_{14}$=H for 2'-deoxy nucleotides, $R_{12}$=H, $R_{14}$=OH for 3'-deoxy nucleotides, and $R_{12}$, $R_{14}$=H in dideoxy nucleotides; $R_9$=H and $CH_3$ in uridine and thymidine, respectively; $R_6$=H and $NH_2$ in inosine and guanidine, respectively.

The six commonly-occurring nucleotides do not absorb light at wavelengths >290 nm and are effectively non-fluorescent under physiological conditions. Derivatives of the commonly occurring N-nucleotides for a variety of synthetic, diagnostic, and therapeutic purposes are common, including substitutions on both the heterocyclic base and the furanose ring. These substitutions can be made at the loci shown in FIG. 2 in which $R_4$ is a reactive group derivatizible with a detectable label (NH, SH, =O, and which can include an optional linking moiety including an amide, thioether, or disulfide linkage or a combination thereof with additional variable reactive groups, $R_1$ through $R_2$, such as $R_1$—$(CH_2)_x$—$R_2$, or $R_1$—$R_2$—$(CH_2)_x$—$R_3$—, where x is an integer in the range of 1 and 25 inclusive); $R_5$ is H or part of an etheno linkage with $R_4$; $R_6$ is H, $NH_2$, SH, or =O; $R_9$ is hydrogen, methyl, bromine, fluorine, or iodine, or an alkyl or aromatic substituent, or an optional linking moiety including an amide, thioether, or disulfide linkage or a combination thereof such as $R_1$—$(CH_2)_x$—$R_2$, or $R_1$—$R_2$—$(CH_2)_x$—$R_3$—, where x is an integer in the range of 1 and 25 inclusive; $R_{10}$ is hydrogen, or an acid-sensitive base stable blocking group, or a phosphorous derivative, $R_{11}$=$R_{12}$=H; $R_{12}$ is hydrogen, OH, or a phosphorous derivative; $R_{14}$ is H, OH, or $OR_3$ where $R_3$ is a protecting group or additional fluorophore. The letter N in the N-nucleosides designates the atom at which the glycosidic covalent bond connects the sugar and the heterocyclic base; in the cases of the commonly occurring nucleosides, the bases are either adenine, guanine, cytosine, inosine, uracil, or thymine; the substituents here and in the fluorescent analogs share the same numbering system for all R groups, but the numbering system for the analog heterocycles does differ for some of the analogs.

Nucleotide sequences are commonly utilized in a variety of applications including diagnostic and therapeutic probes which hybridize target DNA and RNA; and amplification of target sequences. It is often necessary, or useful, to label nucleotide sequences.

1. Labeling of oligonucleotide probes. Hybridization of specific DNA or RNA sequences typically involves annealing oligonucleotides of from as little as 12 bases in length to more than 10,000 bases (10 kb) in length. The majority of oligonucleotide probes currently in research use are radioactively labeled; however, because of (a) the short half lives of the isotopes in common usage, (b) the safety requirements, and (c) the costs of handling and disposal of radioactive probes, convenient and sensitive non-isotopic methods of detection are required for hybridization diagnostic methods to achieve widespread acceptance and application.

In general, all of the non-isotopic methods of detecting hybridization probes that are currently available depend on some type of derivatization of the nucleotides to allow for detection, whether through antibody binding, or enzymatic processing, or through the fluorescence or chemiluminescence of an attached "reporters" molecule. In most cases, oligonucleotides have been derivatized to incorporate single or multiple molecules of the same reporter group, generally at specific cyclic or exocyclic positions. Techniques for attaching reporter groups have largely relied upon (a) functionalization of 5' or 3' termini of either the monomeric nucleosides or the oligonucleotide strands by numerous -chemical reactions using deprotection oligonucleotides in aqueous or largely aqueous media (Cf Cardullo et al. [1988] PNAS 85:8790-8794; also, Chu, B. C. F., G. M. Wahl, L. E. Orgel [1983] Nucl. Acids Res. 11:6513-6529; Kawashima, E. H., A. Chollet [1987] Nucl. Acids Res. 13:1529-1541; Chu, B. C. F., L. E. Orgel [1988] Nucl. Acids Res. 16:3671-3691; Bischoff, R., J. M. Coull, F. E. Regnier [1987] Anal. Biochem. 164:336-344; Ghosh, S. S., P. M. Kao, D. Y. Ywoh [1989] Anal. Biochem. 178:43-51; Zuckermann, R., D. Corey, P. Schulz [1987] Nucl. Acids Res. 15:5305-5321); (b) synthesizing modified nucleosides containing (i) protected reactive groups, such as $NH_2$, SH, CHO, or COOH, (ii) activatable monofunctional linkers, such as NHS esters, aldehydes, or hydrazides, or (iii) affinity binding groups, such as biotin, attached to either the heterocyclic base or the furanose moiety. Modifications have been made on intact oligonucleotides or to monomeric nucleosides which have subsequently been incorporated into oligonucleotides during chemical synthesis via terminal transferase or "nick translation" (Brumbaugh et al. [1988] PNAS 85:5610–5614; Cf also Sproat, B. S., B. Beijer, P. Rider [1987] Nucl. Acids Res. 15:6181–6197; Sproat, B. S., B. Beijer, P. Rider, P. Neuner [1987] Nucl. Acids Res. 15:4837-4848; Jaablonski, E., E. W. Moomaw, R. H. Tullis, J. L. Ruth [1986] Nucl. Acids Res. 14:6115-6128; Sproat, B. S., A. I. Lamond, B. Beijer, P. Neuner, P. Ryder [1989] Nucl. Acids Res. 17:3371-3386; Urdea, M. S., B. D. Warner, J. A. Running, M. Stempien, J. Clyne, T. Horn [1988] Nucl. Acids Res. 16:4937–4956; Allen, D. J., P. L. Darke, S. J. Benkovic [1989] Biochemistry 28:4601–4607; Smith, L. M., S. Fung, M. W. S. Hunkapillar, T. J. Hunkapillar, L. E. Hood [1985] Nucl. Acids Res. 13:2399–2419); (c) use of suitably protected chemical moieties, which can be coupled at the 5' terminus of protected oligonucleotides during chemical synthesis, e.g., 5'-aminohexyl-3'-O-phosphoramidite (Agrawal, S., C. Christodoulu, M. J. Gait [1986] Nucl. Acids Res. 14:6227–6245; Emson, P. C., H. Arai, S. Agrawal, C. Christodoulu, M. J. Gait [1989] Meth. Enzymol.

168:753–761; Arai, H., P. C. Emson, S. Agrawal, C. Christodoulu, M. J. Gait [1988] Molecular Brain Res. 63–69; Connolly, B. A. [1987] Nucl. Acids Res. 15:3131–3139, and references therein; Nelson, P. S., R. S. Gold, R. Leon [1989] Nucl. Acids Res. 17:7177–7186, and references therein; Haralambidis, J., L. Duncan, G. W. Tregar [1990] Nucl. Acids Res. 18:493–499); and, (d) addition of functional groups on the sugar moiety or in the phosphodiester backbone of the polymer (Cf Conway, N. E., J. Fidanza, L. W. McLaughlin [1989] Nucl. Acids Res. Symposium Series 21:43–44; Agrawal, S., P. C. Zamecnik [1990] Nucl. Acids Res. 18:5419–5423).

At the simplest, non-nucleoside linkers and labels have been attached to the 3' or 5' end of existing oligonucleotides by either enzymatic or chemical methods. Modification of nucleoside residues internal to the sequence of a DNA or RNA strand has proven to be a difficult procedure, since the reaction conditions must be mild enough to leave the RNA or DNA oligomers intact and still yield reaction products which can participate in normal Watson-Crick base pairing and stacking interactions.

2. Derivatizations of the heterocyclic base (B). Numerous methods for both cyclic and exocyclic derivatization of the N-nucleoside base have been described, including the following:

(a) Hapten labeling. DNA probes have been amino modified and subsequently derivatized to carry a hapten such as 2,4-dinitrophenol (DNP) to which enzyme-conjugated anti-hapten antibodies bind which subsequently can be processed using a colorimetric substrate as a label (Cf Keller et al. [1988] Analytical Biochemistry 170:441–450).

(b) Amino- and thiol-derivatized oligonucleotides. Takeda and Ikeda ([1984] Nucl. Acids Research Symposium Series 15:101–104) used phosphotriester derivatives of putrescinyl thymidine for the preparation of amino-derived oligomers. Ruth and colleagues have described methods for synthesizing a deoxyuridine analog with a primary amine "linker arm" 12 carbons in length at $C_5$ (Ruth et al. [1985] DNA 4(abstr.):93; Jablonsid et al. [1986] Nucl. Acids Res. 14:6115–6128). These were later reacted with fluorescein to produce a fluorescent molecule. Urdea and Horn were granted a patent in 1990 (U.S. Pat. No. 4,910,300) covering pyrimidine derivatives on which the 6-amino group at $C_4$ had been modified. 3' and 5' amino modifying phosphoramidites have been widely used in chemical synthesis or derivatized oligonucleotides and are commercially available.

(c) Labeling with photobiotin and other biotinylating agents. The high affinity of biotin for avidin has been used to bind enzymatic or chemiluminescent reagents to derivatized DNA probes (Foster et al. [1985] Nucl. Acids Res. 13:745–761). Biotin conjugated to other linkers has also been widely used, including biotin-NHS esters (Bayer, E. A, M. Wilchek [1980] Methods in Biochemical Analysis 26:1), biotin succinamides (Lee, W. T., D. H. Conrad [1984] J. Exp. Med. 159:1790), and biotin maleimides (Bayer, E. A. et al. [1985] Anal. Biochem. 149:529). Reisfeld et al. ([1987] BBRC 142:519–526) used biotin hydrazide to label the 4-amino group of cytidine. A patent was granted to Klevan et al. in 1989 (U.S. Pat. No. 4,828,979) for such derivatizations at the 6-position of adenine, the 4-position of cytosine, and the 2-position of guanine. These derivatizations interfere with hydrogen bonding and base-pairing and have limited uses in producing oligomers for use in hybridization.

(d) dU-Biotin labeling. Nucleoside 5'-triphosphates or 3'-O-phosphoramidites were modified with a biotin moiety conjugated to an aliphatic amino group at the 5-position of uracil (Cf Langer et al. [1981] PNAS 78:6633–6637; Saiki et al. [1985] Science 230:1350–1354). The nucleotide triphosphate derivatives are effectively incorporated into double stranded DNA by standard techniques of "nick translation." Once in an oligonucleotide, the residue may be bound by avidin, streptavidin, or anti-biotin antibody which can then be used for detection by fluorescence, chemiluminescence, or enzymatic processing.

(e) 11-digoxigenin-ddUTP labeling. The enzyme, terminal transferase, has been used to add a single digoxigenin-11-dideoxyUTP to the 3' end of oligonucleotides. Following hybridization to target nucleic acids, DIG-ddUTP labeled hybridization probes were detected using anti-DIG antibody conjugate.

(f) AAIF. Immunofluorescent detection can be done using monoclonal Fab' fragments which are specific for RNA:DNA hybrids in which the probe has been derivatized with, e.g., biotin-11-UTT (Bobo et al. [1990] J. Clin. Microbiol. 28:1968–1973; Viscidi et al. [1986] J. Clin. Microbiol. 23:311–317).

(g) Bisulfite modification of cytosine. Draper and Gold ([1980] Biochemistry 19:1774–1781) introduced aliphatic amino groups onto cytidine by a bisulfite catalyzed termination reaction; the amino groups were subsequently labeled with a fluorescent tag. In this procedure, the amino group is attached directly to the pyrimidine base. Like the derivatization of uracil, these derivatizations interfere with hydrogen bonding and base-pairing and are not necessarily useful for producing efficient hybridization oligomers.

(h) Fluorophore derivatized DNA probes. Texas Red (Sulfochloro-Rhodamine) derivatized probes are commercially available which hybridize to specific target DNAs and which can be detected using a flow cytometer or a microscope (Molecular Analysis, Inc.). Numerous authors have reported coupling fluorophores to chemically synthesized oligonucleotides which carried a 5' or 3' terminal amino or thiol group (e.g., Brumbaugh et al., supra).

(i) Direct enzyme labeling. Chemical coupling of an enzyme directly to a chemically synthesized probe has been used for direct detection through substrate processing. For example, Urdea et al. described an oligonucleotide sandwich assay in which multiple DNA probe hybridizations were used to bind target DNA to a solid phase after which it was further labeled with additional, alkaline phosphatase-derivatized hybridization probes (Urdea et al. [1989] Clin. Chem. 35:1571–1575).

(j) Acridinium ester labeling. A single phenyl ester of methyl acridinium is attached at a central position on an RNA or DNA probe. Hydrolysis of the ester releases an acridone, $CO_2$, and light. Because the ester on unhybridized probes hydrolyzes more quickly than the ester on probes which have hybridized to target RNA or DNA, the chemiluminescence of the hybridized probes can be distinguished from that of free probes and is used in a "hybridization protection assay" (Weeks et al. [1983] Clin. Chem. 29:1474–1479).

3. Derivatizations of the furanose ring (F). Methods for derivatization of the furanose ring ($R_{11}$ through $R_{14}$ in FIG. 3) and at the phosphodiester backbone of oligonucleotides ($R_{10}$ in FIG. 3) have been reported.

(a) Internucleotide linkage reporter groups ($R_{10}$ site). Phosphorothioate esters have been used to provide a binding site for fluorophores such as monobromobimane (Conway et al. [1989] Nucl. Acids Res. Symposium Series 21:43–44). Agrawal and Zamecnik ([1990] Nucl. Acids Res.

18:5419–5423) reported methods for incorporating amine specific reporter groups (e.g., monobromobimane) and thiol specific reporter groups (e.g., fluorescein isothiocyanate) through modifying the phosphodiester backbone of DNA to phosphoramidites and phosphorothioate diesters, respectively.

(b) Glycosidic reporter groups ($R_{11}$ through $R_{14}$ sites). Smith, Fung, and Kaiser ([1989] U.S. Pat. No. 4,849,513) described syntheses for an assortment of derivatives and labels on the glycosidic moiety of nucleosides and nucleoside analogs through the introduction of an aliphatic amino group at $R_{10}$. The authors did not report or claim any uses or applications of inherently fluorescent oligonucleotides, either made chemically or enzymatically or using the fluorescent nucleoside analogs or their derivatives.

4. Fluorescent N-nucleosides and fluorescent structural analogs. Formycin A (generally referred to as Formycin), the prototypical fluorescent nucleoside analog, was originally isolated as an antitumor antibiotic from the culture filtrates of *Nocardia interforma* (Hori et al. [1966] J. Antibiotics, Ser. A 17:96–99) and its structure identified as 7-amino-3-b-D-ribafuranosyl (1H-pyrazolo-[4,3d] pyrimidine)) (FIGS. 5 and 6). This antibiotic, which has also been isolated from culture broths of *Streptomyces lavendulae* (Aizawa et al. [1965] Agr. Biol. Chem. 29:375–376), and *Streptomyces gummaensis* (Japanese Patent No. 10,928, issued in 1987 to Nippon Kayaku Co., Ltd.), is one of numerous microbial C-ribonucleoside analogs of the N-nucleosides commonly found in RNA from all sources. The other naturally-occurring C-ribonucleosides which have been isolated from microorganisms (FIG. 5) include formycin B (Koyama et al. [1966] Tetrahedron Lett. 597–602; Aizawa et al., supra; Umezawa et al. [1965] Antibiotics Ser. A 18:178–181), oxoformycin B (Ishizuka et al. [1968] J. Antibiotics 21:1–4; Sawa et al. [1968] Antibiotics 21:334–339), pseudouridine (Uematsu and Suahdoinik [1972] Biochemistry 11:4669–4674; Heinrikson and Goldwasser [1964] J. Biol. Chem. 239:1177–1187; Suziki and Hochster [1966] Can. J. Biochem. 44:259–272), showdomycin (Nishimura et al. [1964] J. Antibiotics Ser. A 17:148–152; Darnall et al. [1967] PNAS 57:548–553; Nakagawa et al. [1967] Tetrahedron Lett. 4105–4109), pyrazomycin (Gerzon et al. [1969] 2nd Intern. Cong. Heterocyclic Chem.:C-30 (abstract), Montpelier, France; Williams et al. [1969] 158th National Meeting Am. Chem. Soc. (abstract), New York; Sweeny et al. [1973] Cancer Res. 33:2619–2623; Sweeny et al. [1972] Proc. Am. Assoc. Cancer Res. 13:108), and minimycin (Kusakabe et al. [1972] J. Antibiotics 25:44–47; Sasaki et al. [1972] J. Antibiotics 25:151–154). Formycin, formycin B, and oxoformycin B are pyrazopyrimidine nucleosides and are structural analogs of adenosine, inosine, and hypoxanthine, respectively; a pyrazopyrimidine structural analog of guanosine obtained from natural sources has not been reported in the literature. A thorough review of the biosynthesis of these compounds is available in Ochi et al. (1974) J. Antibiotics xxiv:909–916.

(a) Physical properties of the nucleoside analogs. Because several of the C-nucleosides were known to be active as antibiotic, antiviral, or anti-tumor compounds, their chemical derivatization and physical properties have been extensively studied and compared to the structures and syntheses of the N-nucleosides commonly found in DNA and RNA. In the late 1960s, several structural analogs of the six commonly occurring N-nucleosides were found to be fluorescent under physiological conditions; fluorescence in the analogs results from a molecular rigidity of the heterocycle structure itself; not all the structural analogs of a given type, e.g., the C-nucleosides, are fluorescent, nor is fluorescence an exclusive or inherent property of any particular class of structural analogs. Subsequent studies have shown that only a few of the pyrazolo pyrimidines are fluorescent, and that the property is shared with a few other nucleoside derivatives and structural analogs including, but not limited to, several substituted N-nucleosides, azanucleosides, ethenonucleosides, and deazanucleosides, the structures of which can be compared in FIGS. 5–9, to the structures of the six nucleosides in FIG. 1 which are the commonly occurring nucleotides found in DNA and RNA Those surrounded by boxes have been either previously reported or found to be fluorescent during development of the present invention.

Polymers containing fluorescent analogs were prepared by Ward and colleagues for physical studies using then available nucleoside polymerase enzymes (Ward et al. [1969] J. Biol. Chem. 244:3243–3250; Ward et al. [1969] loc cit 1228–1237). There have been no recent reports in the literature of attempts to combine the use of fluorescent nucleosides or their structural analogs with the synthesis or hybridization techniques of molecular biology or to synthesize fluorescent oligonucleotides therefrom.

5. Limitations of non-isotopic methods for labeling oligonucleotides. In order to create non-radioactive types of detectable oligonucleotides, it has been necessary to chemically modify the nucleosides typically used in DNA and RNA probes, which has made such probe preparation expensive and laborious; in many cases the detection chemistries have also proven cumbersome and expensive to use, which has largely been responsible for their failure to find significant application in clinical laboratories. In their applications to hybridization, other limitations of chemically derivatized probes have also become apparent.

(a) Chemically derivatized dNTPs are generally not cost-effective for use as stock deoxynucleotide triphosphates in PCR amplification, hence, labeling of amplified DNA is limited to (i) amplification using previously labeled primers, or (ii) annealing with labeled hybridization probes. Use of the former frequently results in false positives during amplification owing to non-specific annealing of primers to non-target segments of DNA during amplification. Expense and technical difficulties in post-hybridization processing have largely limited the applications of labeled hybridization probes to research.

(b) Base pairing is hindered for many oligomers made with derivatized nucleosides through the introduction of bulky or non-hydrogen bonding bases at inappropriate sites in a sequence. Owing to the inherent background chemiluminescence of many clinical samples, even the acridinium ester probes have failed to achieve their theoretical levels of sensitivity. The requirements for post hybridization processing have remained a limitation to such methods.

(c) It has proven difficult to provide non-radioactively labeled probes which may be inexpensively produced in large quantities.

(d) Chemiluminescent probes are short lived and samples so tested are difficult to quantify or to "reprobe" accurately.

(e) Hybridization in most cases is only inferred, is non-quantitative or only semi-quantitative, and is non-automatable.

These limitations have hindered applications of DNA and RNA hybridization probes to clinical laboratory testing and therapeutic uses.

BRIEF SUMMARY OF THE INVENTION

The subject invention pertains to nucleoside analogs which are fluorescent. The invention further pertains to the use of these fluorescent nucleotides which can be substituted for naturally occurring nucleosides in the synthesis of oligonucleotide probes. When used as hybridization probes, the fluorescence of such oligonucleotides can be used as a diagnostic tool to detect and identify specific genetic sequences. This methodology is distinct from other non-radioactive methods of probe detection in that it does not utilize nucleotides which have been coupled to enzymes or other reactive proteins and does not require post-hybridization processing for the detection of hybridization.

As described in the Background section, there are many shortcomings to the methods and compositions currently used in DNA and RNA probe technology. It is an object of the present invention to overcome these shortcomings of the prior art through the use of fluorescent nucleosides and their fluorescent structural analogs which can be directly incorporated into a prescribed sequence as (i) specific substitutes for a given nonfluorescent nucleotide which appear at defined locations in the complementary sequences to template or target DNA, and (ii) as labels for the identification and detection of specific sequences of template, product, amplified, or target DNA and/or RNA.

It is another object of the present invention to provide novel, inherently fluorescent nucleoside and nucleoside analogs useful in the synthesis of labeled polynucleotide probes, amplimers, diagnostics, and therapeutics. It is a further object of the present invention to provide methods of making autofluorescent oligonucleotides capable of specific Watson-Crick base pairing with prescribed sequences of target DNA or RNA.

It is another object of the invention to provide methods of using fluorescent nucleoside analogs and oligonucleotides made therefrom and synthesized according to the methods of the present invention to identify, detect the presence of, and/or alter the function of known nucleic acid sequences of DNA and RNA. Additionally, it is an object to improve and simplify the methods of detection, and to simplify the applications and uses of DNA and RNA hybridization techniques.

In one aspect of the invention, fluorescent structural analogs of the commonly occurring nucleosides and their derivatives useful in the synthesis, labeling, and detection of oligonucleotides are provided having the structural formulae of FIGS. 5 through 9. The commonly occurring nucleosides characteristically form hydrogen bonds in a specific donor/acceptor relationship, designated Watson-Crick base pairing as shown in FIG. 4. Where appropriate, specific fluorescent nucleoside analogs capable of reproducing the pattern of Watson-Crick hydrogen bond formation analogous to that of a particular commonly occurring nucleoside are provided, as indicated for, e.g., A:T and formycin:T in FIG. 4 by the donor/acceptor patterns.

In another aspect of the invention, methods of making and derivatizing the fluorescent structural analogs of the commonly occurring nucleosides are provided including the steps of derivatizing the $R_{10}$, $R_{12}$, and $R_{14}$ moieties to be (i) reactive in DNA or RNA synthesis, and/or (ii) reactive in Resonance Energy Transfer of the fluorescence from the structural analogs.

In still another aspect, methods of synthesizing and using polynucleotide probes are provided using one or more of the fluorescent structural analogs and/or their derivatized forms. Such probes can be used to screen a sample containing a plurality of single stranded or double stranded polynucleotide chains and will label, detect, and identify the desired sequence, if present, by hybridization. It is an important aspect of the invention that the fluorescent oligonucleotide probes can be used with "solution hybridization" methods as depicted in FIGS. 11 and 12.

In accordance with the foregoing objects, the present invention comprises inherently fluorescent nucleosides which can be used to label, modify, or identify oligonucleotides made therefrom, the uses of such inherently fluorescent oligonucleotides as hybridization probes, and methods for detecting nucleotide sequences.

Additional formulae, advantages, methods of use, and novel features of the invention will be set forth in the description which follows, and in part become apparent to those skilled in the art after examination of the following, or may be learned by practice of the invention.

BRIEF DESCRIPTION OF THE SEQUENCES

SEQ ID NO. 1 is a synthetic oligonucleotide according to the subject invention.

SEQ ID NO. 2 is a synthetic oligonucleotide and the complement of SEQ ID NO. 1.

SEQ ID NO. 3 is a synthetic oligonucleotide and a fluorescent analog of SEQ ID NO. 2.

DETAILED DISCLOSURE OF THE INVENTION

Disclosed and claimed are novel fluorescent nucleoside analogs and methods of use of the fluorescent nucleosides in, for example, nucleic acid probes and diagnostic kits. One preferred embodiment pertains to the use of inherently fluorescent nucleoside analogs in the chemical and enzymatic synthesis of DNA hybridization probes including solid phase synthesis, template directed enzymatic polymerization and amplification using polymerase chain reaction methods. Another embodiment relates to the use of autofluorescent DNA hybridization probes in the detection and diagnosis of infectious and genetic diseases.

Specifically, the subject invention pertains to nucleoside analogs which are fluorescent and which can be substituted for naturally occurring nucleosides in the synthesis of oligonucleotide probes. When used as hybridization probes, the fluorescence of such oligonucleotides can be used in a variety of procedures to detect and identify specific genetic sequences. This methodology is distinct from other non-radioactive methods of probe detection in that it does not utilize nucleotides which have been coupled to enzymes or other reactive proteins. Thus, described herein are applications of inherently fluorescent nucleoside analogs in developing hybridization techniques for routine, automatable clinical diagnosis.

The fluorescent analogs of the subject invention are of three general types: (A) C-nucleoside purine analogs; (B) N-nucleoside analogs; and (C) N-azanucleotide analogs. All of these compounds have three features in common: 1) they are structural analogs of the common nucleotides capable of replacing naturally occurring nucleosides in enzymatic or chemical synthesis of oligonucleotides; 2) they are naturally fluorescent when excited by light of the appropriate wavelength(s) and do not require additional chemical or enzymatic processes for their detection; and 3) they are spectrally distinct from the nucleosides commonly encountered in naturally occurring DNA.

Figure 1:
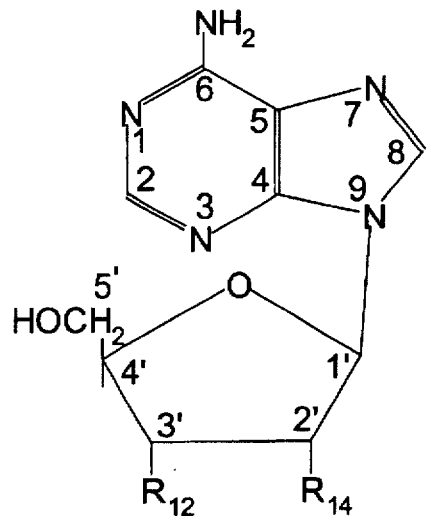
FIG. 1 shows the six commonly-occurring N-nucleosides which predominate in DNA and RNA.
Figure 1:
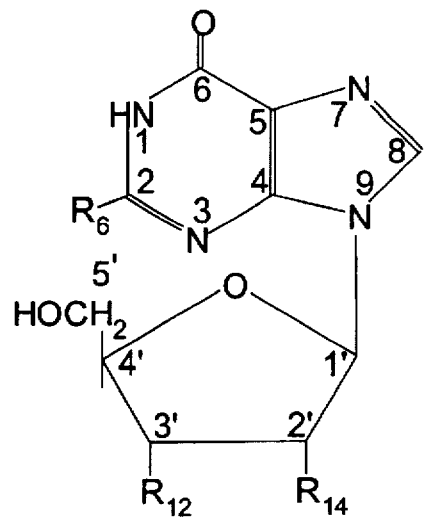
Figure 1:
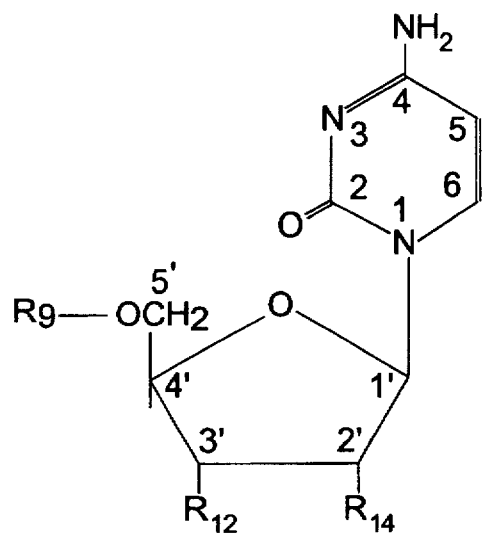
Figure 1:
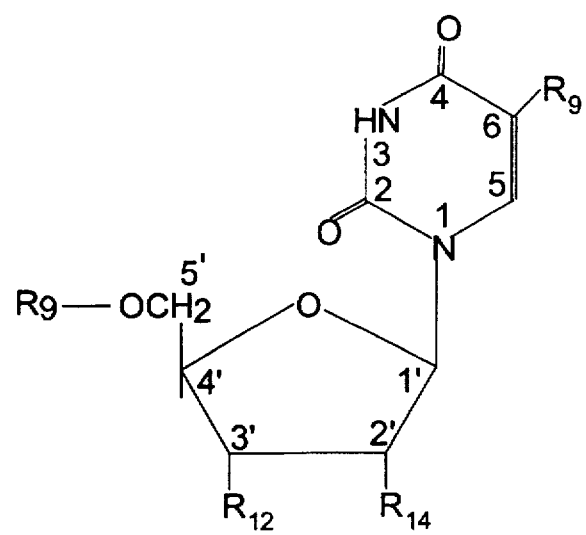

Definitions. The following definitions are provided for ease in understanding the description:

"Commonly Occurring Nucleosides" are the six monomeric N-nucleotides shown in FIG. 1, which predominate in naturally occurring DNA and RNA, enter into classical Watson-Crick base pairing, and are effectively non-fluorescent under physiological conditions. The respective one-letter symbols in sequence shorthand are A, C, G, T, U, and I for adenosine, cytidine, guanidine, thymidine, uridine, and inosine, respectively.

Figure 4A:
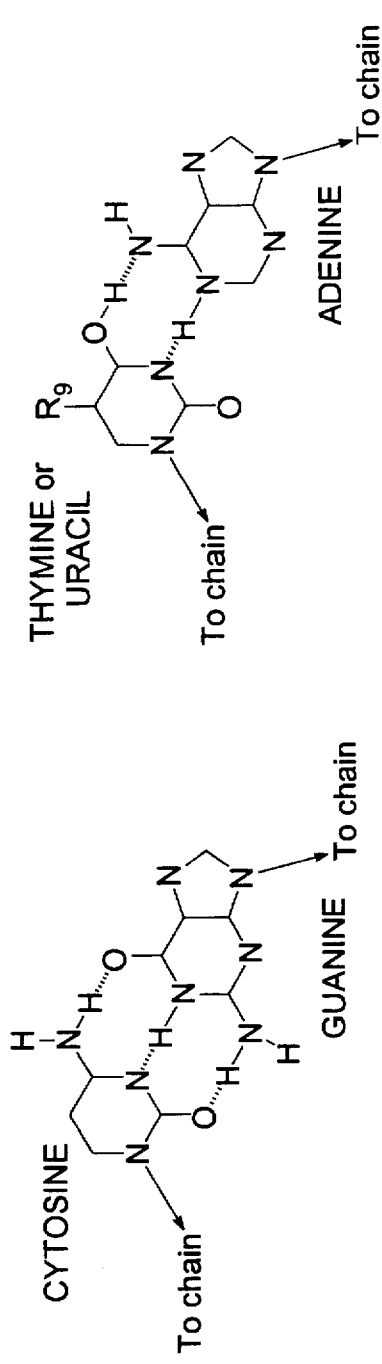
FIG. 4A shows Watson-Crick base pairing between the normally occurring N-nucleotides A:T and G:C.
Figure 4B:
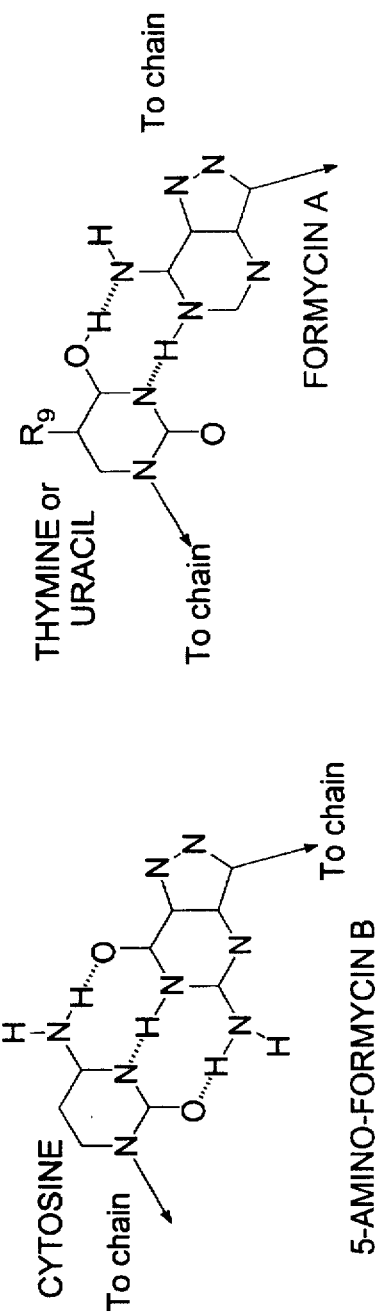
FIG. 4B shows base pairing between formycin:T, formycin:U, 2,6-diaminopurine:T, and 5-amino-formycin B:C.
Figure 5:
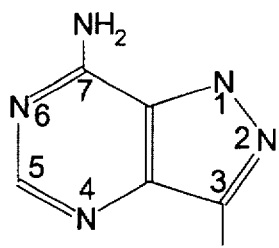
FIG. 5 shows structural analogs of the commonly-occurring N-nucleotides derived from biological sources.
Figure 5:
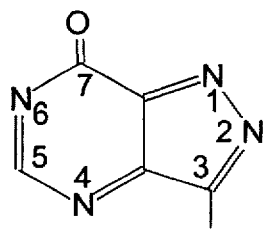
Figure 5:
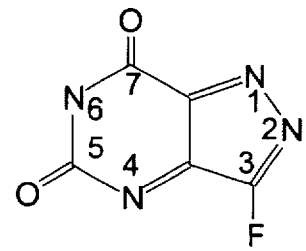
Figure 5:
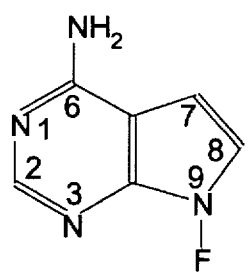
Figure 5:
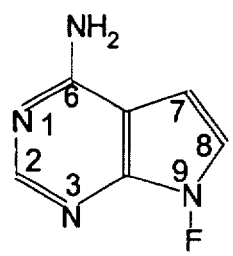
Figure 5:
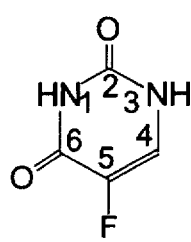
Figure 5:
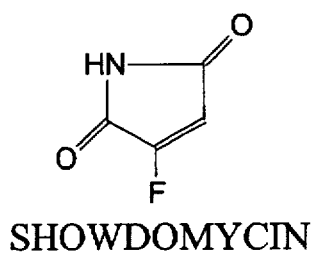
Figure 5:
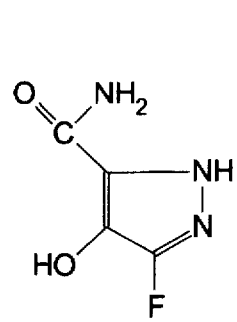
Figure 5:
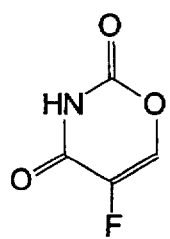
Figure 6:
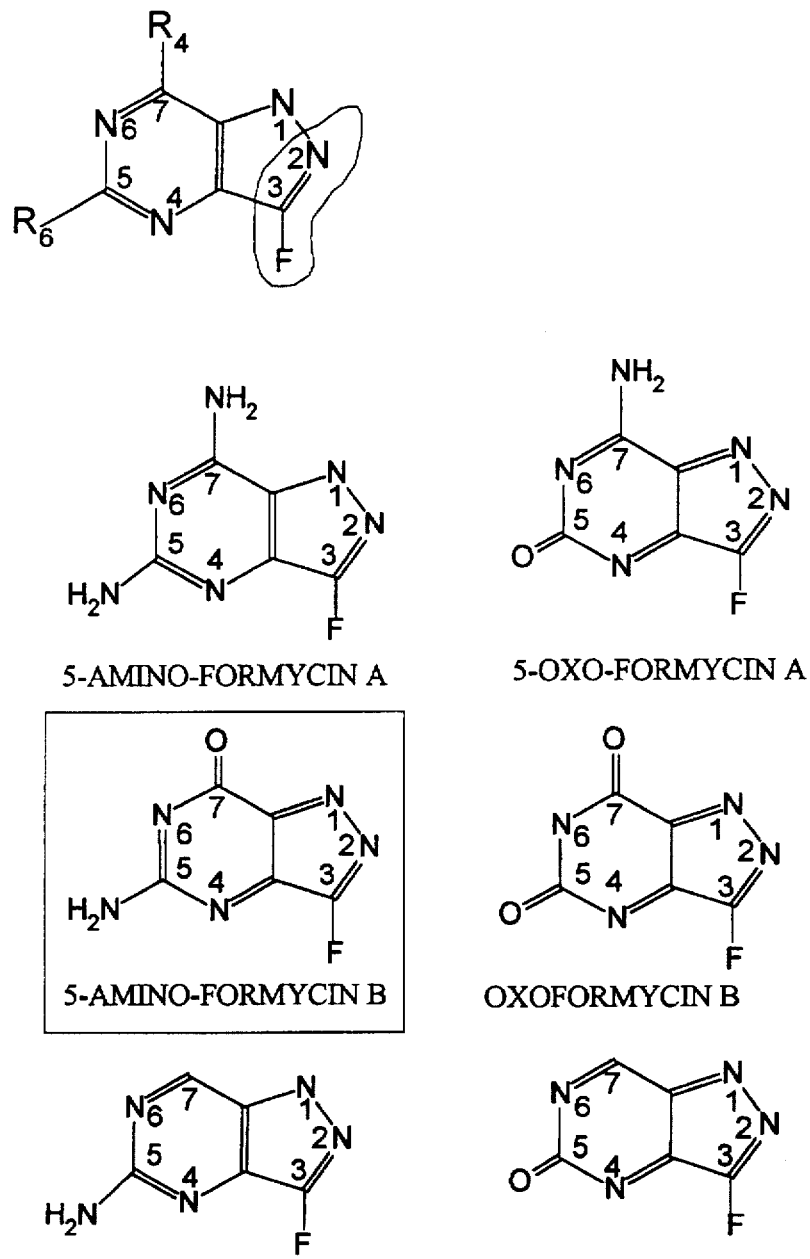
FIG. 6 shows the pyrazolo [4,3d] pyrimidine nucleoside analogs.
Figure 7:
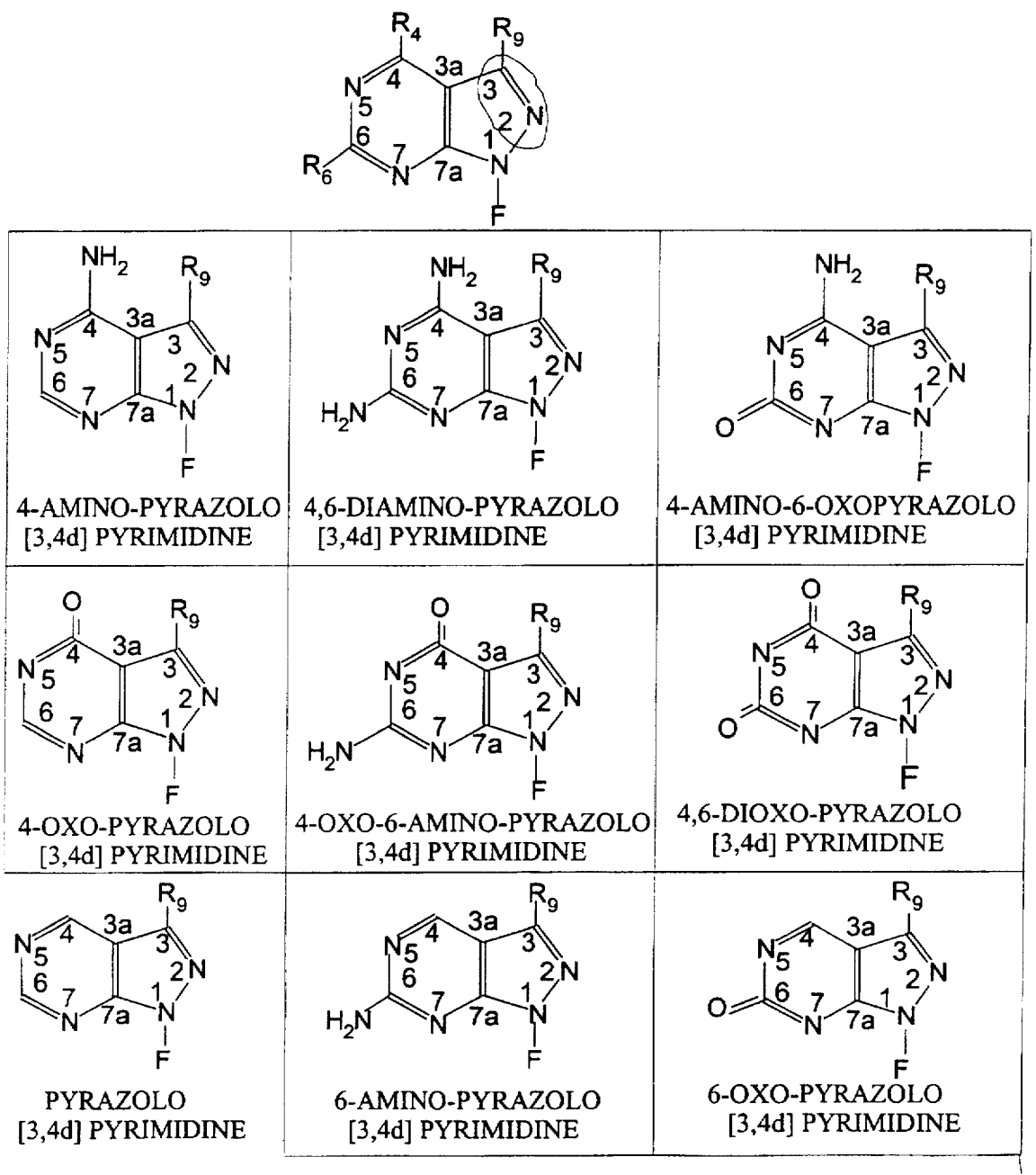
FIG. 7 shows the pyrazolo [3,4d] pyrimidine nucleoside analogs.
Figure 8:
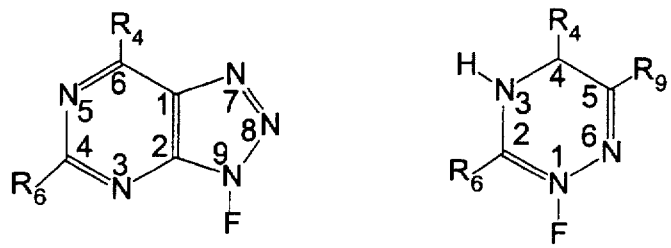
FIG. 8 shows the azapyrimidine and azapurine nucleoside analogs.
Figure 8:
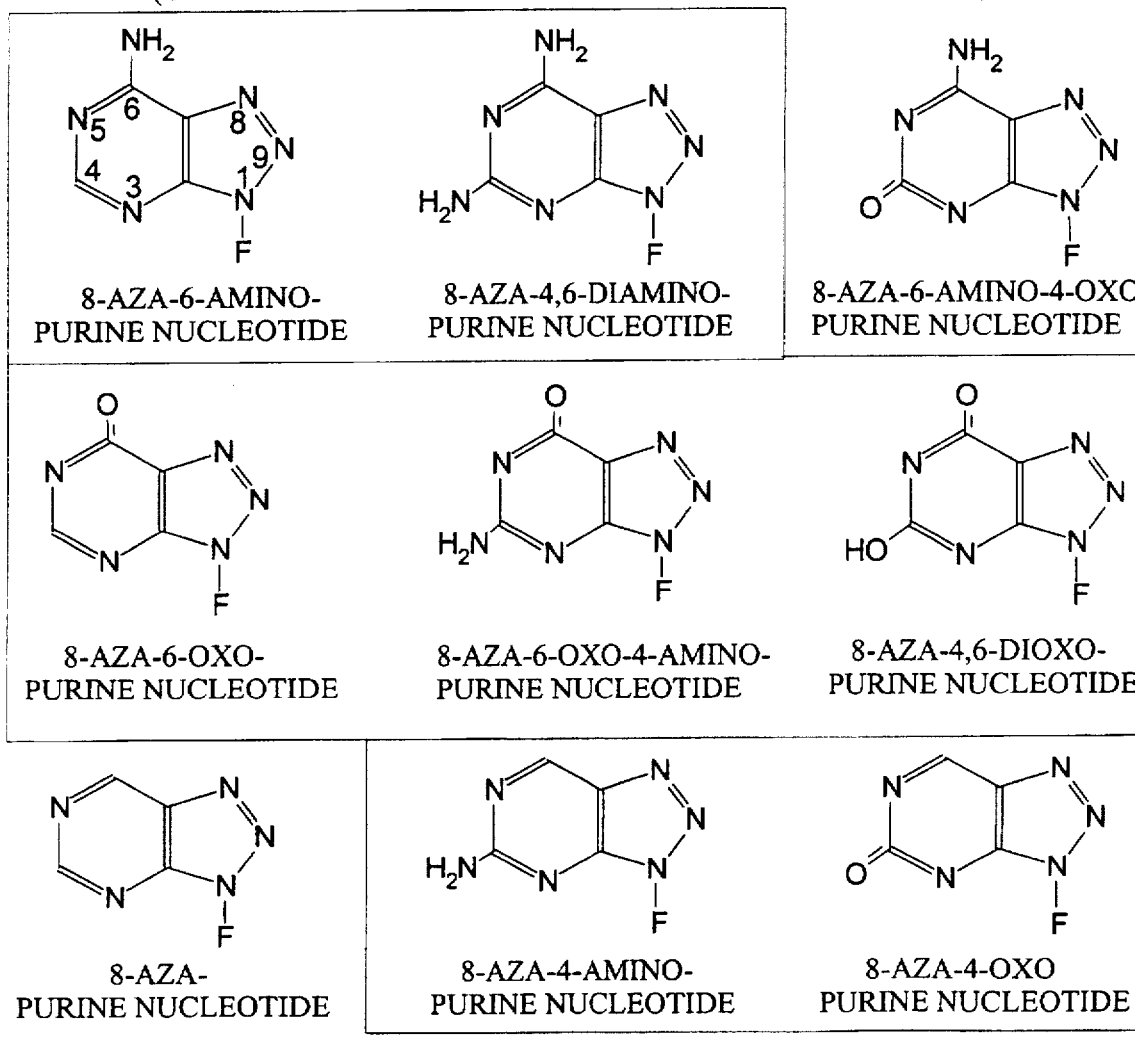
Figure 9A:
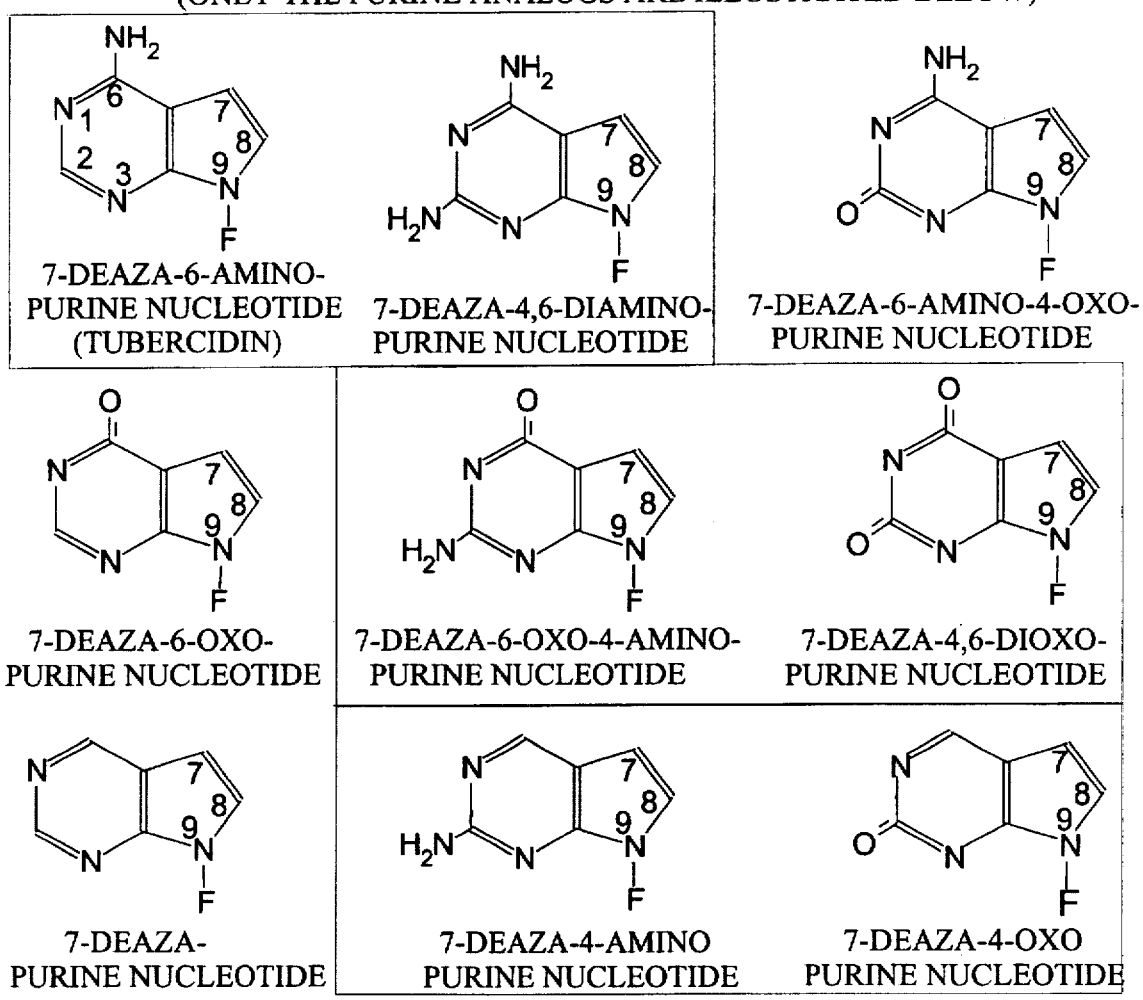
FIGS. 9A–B shows the deazapyrimidine and deazapurine nucleoside analogs.
Figure 9B:
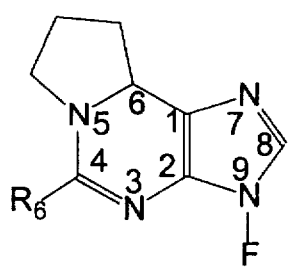
Figure 9B:
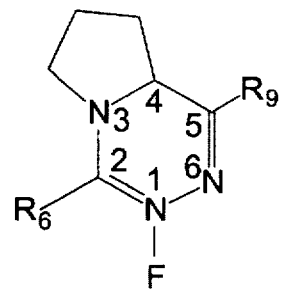
Figure 9B:
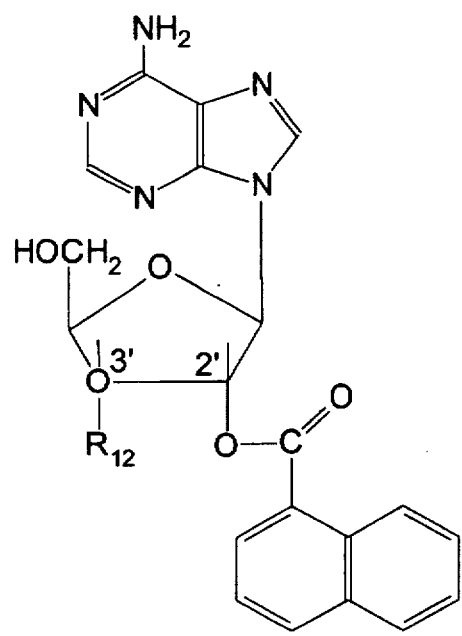
Figure 9B:
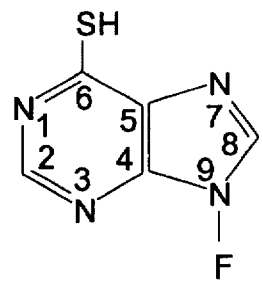

"Structural Analogs" of the commonly occurring nucleosides are structurally related molecules that mimic the normal purine or pyrimidine bases in that their structures (the kinds of atoms and their arrangement) are similar to the commonly occurring bases, but may have certain modifications or substitutions which do not affect basic biological activity or biochemical functions. Such base analogs include, but are not limited to, imidazole and its 2,4- and/or 5-substituted derivatives; indole and its 2-, 3-, 4-, 5-, 6-, and/or 7-substituted derivatives; benmimidazole and its 3-, 4-, and/or 5-substituted derivatives; indazole and its 3-, 4-, 5-, 6-, and/or 7- substituted derivatives; pyrazole and its 3-, 4-, and/or 5-substituted derivatives; triazole and its 4- and/or 5-substituted derivatives; tetrazole and its 5-substituted derivatives; benzotriazole and its 4-, 5-, 6-, and/or 7-substituted derivatives; 8-azaadenine and its substituted derivatives; 6-azathymine and its substituted derivatives; 6-azauracil and its substituted derivatives; 5-azacytosine and its substituted derivatives; 8-azahypoxanthine and its sub-stituted derivatives; pyrazolopyrimidine and its substituted derivatives; 3-deazauracil; orotic acid; 2,6-dioxo-1,2,3,6-tetrahydro-4-pyrimidine carboxylic acid; barbituric acid; uric acid; ethenoadenosine; ethenocytidine; an allopurinol (4-hydroxy-pyrazolo [3.4d] pyrimidine); or their protected derivatives as described below. B can also be any of the C-nucleosides such as are shown in FIGS. 5 and 6 in which the normal C—N bond between the base and the furanose ring is replaced by a C—C bond; such bases include, but are not limited to, uracil, as in the C-nucleoside pseudouridine; 1-methyluracil; 1,3-dimethyluracil; 5(4)-carbomethoxy-1,2, 3-triazole; 5(4)-carboxamido-1,2,3-triazole; 3(5)-carboxymethylpyrazole;3(5)-carbomethoxypyrazole;5-carboethoxy-1-methylpyrazole; maleimide (in the C-nucleoside showdomycin); and 3(4)-carboxamido-4(3)-hydroxypyrazole (in the C-nucleoside pyrazomycin); and any of the other analogs listed or inferred in FIGS. 4 through 9; or their protected derivatives.

"Fluorophore" refers to a substance or portion thereof which is capable of emitting fluorescence in a detectable range. Typically of the fluorescent structural analogs of the nucleotides, this fluorescence typically occurs at wavelengths in the near ultraviolet (>300 nm) through the visible wavelengths.

"Fluorescent Structural Analogs" are synthetic or biochemically derived monomeric structural analogs of the six commonly occurring N-nucleosides (FIG. 1), such as are depicted in FIGS. 4 through 9, which may or may not be capable of classical Watson-Crick base pairing depending upon the monomeric structure and/or oligonucleotide in which they are used, but which are spectrally unique and distinct from the commonly occurring nucleosides in their capacities for selective excitation and emission under physiological conditions. For example, the C-nucleoside formycin A is a structural analog of adenosine that can form equivalent donor/acceptor hydrogen bonds, but which has an excitation maximum in oligonucleotides at 312 nm and an emission maximum at 405 nm (Stokes Shift=93 nm).

"Derivatized" nucleoside analogs are fluorescent structural analogs in which reactive or protective functional groups are bound, covalently or otherwise, at the $R_4$ through $R_9$ positions of the heterocycle and/or the $R_{10}(5')$, the $R_{12}(3')$, and $R_{14}(2')$ positions of the glycosidic moiety. Derivatives at the 2' glycosidic position may include fluorescence resonance energy transfer (FRET) acceptors or donors which enhance or accept and re-emit at longer wavelengths the inherent fluorescence emission of the fluorescent structural analog itself.

A "polynucleotide," "oligonucleotide," or "oligomer" is a nucleotide chain structure containing at least two commonly occurring nucleotides or fluorescent structural analogs. The "fluorescent oligonucleotide probe" or "fluorescent hybridization probe" provided herein is a nucleotide chain structure, as above, containing at least two monomers, at least one of which is fluorescent.

"Hybridization" is the pairwise annealing through Watson-Crick base pairing of two complementary, single-stranded molecules (Cf FIG. 4), which may be DNA:DNA, DNA:RNA, or RNA:RNA, and in which the two strands may come from different sources. The annealing is specific (i) for complementary base pairs in which the hydrogen bond donors and acceptors are oriented as in FIG. 4, and (ii) for the complementary genetic sequence of the specific gene, target DNA, or target RNA (hereinafter "target DNA/RNA") to which the probe is to be hybridized. Compare, for example, the hydrogen bond pattern of adenosine and formycin (FIG. 4).

"DNA/RNA Melting Temperature" and "Tm" refer to the temperature at which the hydrogen bonds between hybridized strands of DNA or RNA are disrupted and the strands disassociate into single strands, thereby disrupting the structure of the duplex or hybrid.

"Analogous fluorescent sequence" refers to the nucleoside sequence of a polynucleotide which has been synthesized by any of the enzymatic or chemical methods described in the present invention, but in which fluorescent nucleoside analogs have been explicitly substituted for particular commonly occurring nucleosides, e.g., the substitution of formycin-5'-triphosphate (FTP) for adenosine-5'-triphosphate (ATP), when using RNA polymerase to produce RNA probes complementary to a prescribed DNA template. In an analogous fluorescent sequence, the fluorescent nucleoside analog has been substituted in the oligonucleotide chain at, and only at, every position in which the corresponding commonly occurring nucleotide would have occurred in the sequence as dictated by, e.g., the template, in the case of enzymatic synthesis. Similar programmed substitutions can be made using 3'-O-phosphoramidites of the individual fluorescent analogs during standard phosphotriester synthesis. Thus, for example, the complementary sequence of the MOMP gene, or its fluorescent analogous sequence, can be synthesized enzymatically using dATP or dFTP, respectively, in the presence of DNA polymerase, dCTP, dTTP, and dGTP:

MOMP GENE SEQUENCE SEQ ID NO: 1:
AAC GTT CGA GAC GGA CAC CCC TTA GGA CGA CTT GGT TCG

COMPLEMENT SEQUENCE SEQ ID NO: 2:
TTG C<u>AA</u> GCT CTG CCT GTG GGG <u>AA</u>T CCT GCT G<u>AA</u> CCA <u>A</u>GC

ANALOGOUS FLUORESCENT SEQUENCE SEQ ID NO: 3:
TTG C<u>FF</u> GCT CTG CCT GTG GGG <u>FF</u>T CCT GCT G <u>FF</u> CC<u>F</u> <u>F</u>GC wherein the fluorescent deoxyformycin (<u>F</u>) residues underlined in the analogous sequence are the structural analogs of the deoxyadenosine (<u>A</u>) residues in the same relative positions in the complementary sequence.

"FRET acceptor" or "Fluorescence Resonance Energy Transfer acceptor" refers to a substance, substituent, chromophore, or fluorophore, e.g., a dansyl, naphthyl, anthryl, pyrenyl, methylumbelliferone, or coumarin moiety, which is capable of absorbing emitted light from fluorescent structural analog donors and re-emitting that energy at other, longer wavelengths. In the context of the present invention, such secondary fluorophores may be selectively excited as a second label, or may be used as a fluorescence acceptor to broaden and enhance the primary fluorescence of the structural analog energy donor.

A. Structures, Sources, Synthesis, and Derivatization of the Fluorescent Nucleoside Analogs Briefly, the present invention includes the heterocyclic pyrimidine or purine structural analogs of the commonly occurring nucleoside bases (B) which are fluorescent under physiological conditions and which are linked by a carbon-carbon or carbon-nitrogen bond to the set of furanose rings (designated F in FIGS. 4–9) of ribose ($R_{12}$=$R_{14}$=OH), deoxyribose ($R_{12}$=H, $R_{14}$=OH, or $R_{12}$=OH, $R_{14}$=H), or dideoxyribose ($R_{12}$=$R_{14}$=H) and their derivatives such as are described below, and/or are apparent to one familiar with nucleotide chemistry.

For the present invention, formycin, 2-amino purine ribonucleoside, and 2,6-diamino nbonucleoside, all of which can (i) form the same or related base-pairing hydrogen bonds as adenosine, and (ii) substitute specifically for adenosine in Watson-Crick base pairing as well as in a wide variety of enzymatic reactions including nucleic acid replication, ligation, and phosphorylation, are used as representatives of the set of fluorescent nucleosides and nucleoside analogs (FIG. 4). Related properties and parallel claims obtain in the present invention for all other fluorescent analogs of guanosine, cytidine, thymidine, uridine, inosine, and their derivatives.

1. Structures of the nucleoside analogs. The generic purine and pyrimidine structures of each type of structural analog to the commonly occurring nucleosides are given at the top of each of FIGS. 5 through 9, below which are representative examples of each class of analog. Only examples of the purine analogs are given in FIGS. 6 and 7, since the known pyrimidine analogs have already been illustrated in FIG. 5. With the exception of the N-nucleoside analogs, which have only substitutions at $R_4$, $R_6$, and $R_9$, the generic structures at the top of each page have a gray oval indicating the substitutions to the heterocyclic base which distinguish the analog from the commonly occurring N-nucleosides shown in FIG. 1.

Figure 2:
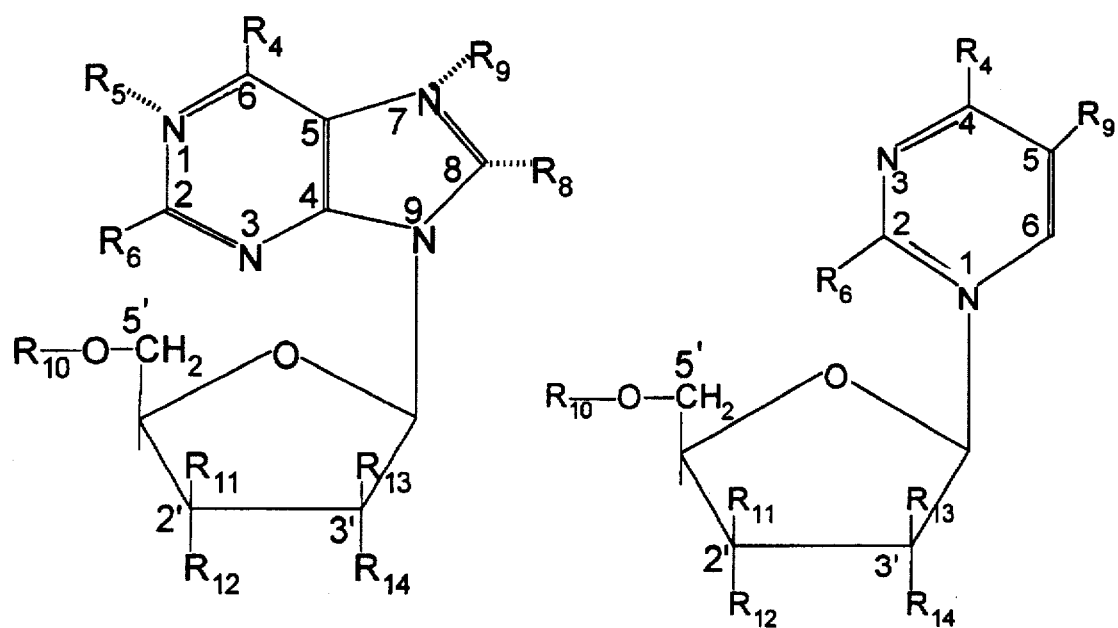
FIG. 2 shows the general structures of the commonly-occurring N-nucleosides and their derivatization sites, $R_n$.
Figure 3:
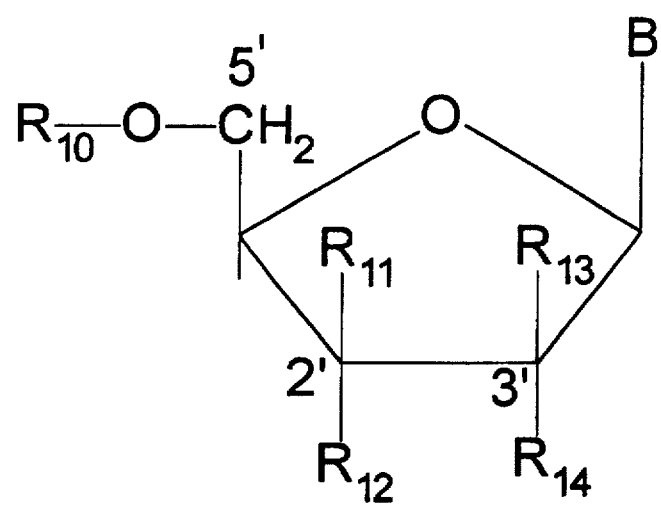
FIG. 3 shows the general structure of the furanose ring of both the purine and pyrimidine nucleosides and the common sites, $R_n$ for derivatization.

2. Furanose moieties common to the fluorescent nucleoside analogs. The numbering of the sugar carbon atoms in furanose is 1' to 5' is indicated in FIG. 2, thus the base, B, is connected to C1 of the sugar. The furanose moiety of any fluorescent heterocycle claimed in this invention has, in common with all other analogs, the set F, of glycosides and substituted glycosides, as follows: substitutions can be made, in principle, at any of the 5 sugar carbons; the subset F is defined by derivatives and/or substitutions at positions $R_{10}$, $R_{11}$, $R_{12}$, $R_{13}$, and $R_{14}$, which (i) are obvious to one skilled in the art, and (ii) are the furanosyl derivatives of all the fluorescent nucleoside analogs claimed in the present invention. These include all phosphorous substitutions (e.g., triphosphate, thiophosphate, aminophosphate, etc.) and all protecting substitutions (e.g., dimethoxytrityl) at position $R_{10}$. For all glycosides, F, in FIGS. 5 through 9, $R_{10}$, $R_{11}$, $R_{12}$, $R_{13}$, and $R_{14}$ are defined as follows: $R_{11}$ and $R_{13}$=H; $R_{14}$=H, OH, or $OR_i$; $R_{12}$ and $R_{10}$ are either H, OH, $OR_m$, or $NHR_k$, wherein (a) $R_i$ protecting groups are generally a lower aryl or alkyl ether, such as methyl, t-butyl, benzyl, o-nitrobenzyl, p-nitrobenzyl, o-nitrophenyl, or triphenylmethyl; or a lower alkyl or aryl ester such as acetyl, benzoyl, or p-nitrobenzoyl, or an alkyl; acetal such as tetrahydropyranyl; or a silyl ether, such as trimethylsilyl or t-butyldimethylsilyl; or a sulfonic acid ester such as p-toluenesulfonyl or methanesulfonyl; or halide such as bromine, fluorine, or iodine. Additional examples of suitable blocking groups may be found in Green, T. W. (1981) *Protective Groups in Organic Synthesis*, New York: Wiley & Sons. Alternatively, $R_{14}$ may be a FRET derivative including, but not limited to, such fluorophores as 7-[3-(chlorodimethylsilyl)propoxy]-4-methylcoumarin, O-4-methylcoumarinyl-N-[3-triethoxysilyl)propylcarbamate, and N-3-triethoxysilylpropyl)dansylamide; (b) $R_m$ represents an appropriate protecting, substituting, or reactive linker group including 2' or 3'-amido, 2' or 3'-azido, 2',3'-unsaturated, and the subset of phosphorous derivatives involved in chemical or enzymatic syntheses of oligonucleotides having a phosphate ester, thiophosphate ester, or aminophosphate ester backbone; (c) $R_k$ is any common, standard nitrogen protecting group, such as those commonly used in peptide synthesis (Geiger, R., W. Konig [1981] In *The Peptides: Analysis, Synthesis, Biology*, Vol. 3, E. Gross, J. Meienhofer, eds., Academic Press, New York, pp. 1–99); this includes, but is not limited to, acid-labile protecting groups such as formyl, t-butyloxycarbonyl, benzyloxycarbonyl, 2-chlorobenzyloxycarbonyl, 4-chlorobenzyloxycarbonyl, 2,4-dichlorobenzyloxycarbonyl, furyfuryloxycarnonyl, t-amyloxycarbonyl, adamantyloxycarbonyl, 2-phenylpropyl-(2)-oxycarbonyl, 2-(4-biphenyl)propyl-(2)-oxycarbonyl, triphenylmethyl, p-anisyldiphenylmethyl, di-p-anisyl diphenylmethyl, 2-nitrophenylsulfenyl, or diphenylphosphinyl; base labile protecting groups such as trifluoroacetyl, 9-fluorenylmethyloxycarbonyl, 4-toluenesulfonylethyloxycarbonyl, methylsulfonylethyloxycarbonyl, and 2-cyano-t-butyloxycarbonyl; as well as others, such as chloroacetyl, acetoacetyl, 2-nitro-benzoyl, dithiasuccinoyl, maleoyl, isonicotinyl, 2-bromoethyloxycarbonyl, and 2,2,2-trichloroethyloxycarbonyl; alternatively, $R_k$ may also be any reactive group derivatizible with a detectable label ($NH_2$, SH, =O, and which can include an optional linking moiety including an amide, thioether or disulfide linkage, or a combination thereof with additional variable reactive groups $R_1$ through $R_2$, such as $R_1-(CH_2)_x-R_2$, where x is an integer in the range of 1 and 8, inclusive) or any linker or spacer functioning as a homobifunctional or heterobifunctional linker including, but not limited to, such reactive groups as hydrazides, maleimidazoles, oxidizable diols, and succinimydyl groups. At most only one of $R_{12}$ and $R_{10}$ may be $NHR_k$.

The invention further includes novel phosphoramidites having the formula:

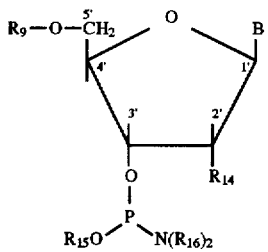

wherein B is any of the fluorescent nucleoside analogs described herein and $R_{14}$ may be either H or OH. $R_{16}$=lower alkyl, preferably lower alkyl such as methyl or isopropyl, or heterocyclic, such as morpholino, pyrrolidono, or 2,2,6,6-tetramethylpyrrolidono; $R_{15}$=methyl, beta-cyanoethyl, p-nitrophenyl, o-chloronitrophenyl, or p-chlorophenyl. All other R groups are as before including those identifying spacer or linker arms of from 1 to 25 carbon atoms in length. The moiety B in the phosphoramidite must also be protected prior to the synthesis of the phosphoramidite in order to (i) preserve any reactive substituents on the heterocycle which are important to its participation in Watson-Crick base pairing, and (ii) render the amidite compatible with the DNA or RNA chain assembly chemistry. Protection generally involves acylation or amidation of the exocyclic amino groups and includes, but is not limited to, acetyl, benzoyl, isobutryl, succcinyl phthaloyl, or p-anisoyl; such amidine groups include, but are not limited to, dimethylformamidine, di-n-butylformamidine, or dimethylacetamidine; if B is substituted with other reactive groups such as carboxyl, hydroxyl, or mercapto, these are appropriately protected as well.

The present invention encompasses the synthesis of oligonucleotides on a solid phase support, wherein the oligomer is reacted with the protected fluorescent nucleoside analog phosphoramidites as illustrated in FIGS. 4 through 9 and derivatized as in the structure, above. Additionally, the present invention includes the novel fluorescent oligonucleotides having included in their sequences at least one fluorescent nucleoside analog derivatized as the phosphoramidite in the structure, above. Moreover, it is yet again another aspect of the present invention to provide fluorescent oligonucleotides made by the reactions of the aforementioned fluorescent analog 3'-O-phosphoramidites which are bound to, or have been bound by, a solid support.

3. Sources and other preparations of the fluorescent structural analogs. Formycin A (hereinafter referred to simply as formycin) is isolated as the ribonucleotide from the culture broths of *Nocardia interforma*. The antibiotic is also isolated from culture broths of *Streptomyces lavendulae* and *Streptomyces gummaensis*, and is one of numerous microbial C-ribonucleoside analogs of the N-nucleosides commonly found in RNA from all sources. The other naturally occurring C-ribonucleosides which have been isolated from microorganisms (FIGS. 4 through 9) include formycin B, oxoformycin B, pseudouridine, showdowmycin, pyrazomycin, and minimycin. Formycin, formycin B, and oxoformycin B are C-nucleosides or pyrazopyrimidine nucleosides of the class shown in FIG. 6 and are structural analogs of adenosine, inosine, and hypoxanthine, respectively; a pyrazopyrimidine structural analog of guanosine obtained from natural sources has not been reported in the literature but can be chemically synthesized from the 2-chloro-formycin B or its deoxy form. A thorough review of the biosynthesis of these compounds is available in Ochi et al. (1974) J. Antibiotics xxiv.:909–916. Synthesis of the $N_4$ and $N_6$ derivatives of the C-nucleotides are described in Lewis and Townsend ([1980] J. Am. Chem. Soc. 102:2817). Corresponding syntheses for the isomeric aminopyrazolo-[3,4d]-pyrimidines are in Wierchowski et al. (all others are commercially available in ribose, and several in deoxy and dideoxy forms, including the azanucleotides and deaza nucleotides, or can be synthesized de novo, e.g., 7-deazaadenine (Gerster et al. [1967] J. Med. Chem. 10: 326)).

(a) Production of the deoxy, dideoxy, and phosphorylated forms of the fluorescent ribonucleoside analogs. Chemical syntheses are available in the literature for the derivatization as 2'-deoxy forms and 3'-deoxy forms of N-nucleoside, ethenonucleosides as well as the C-nucleosides (Robins et al. [1973] Can. J. Chem. 51:1313; Jain et al. [1973] J. Org. Chem. 38:3719; DeClerq et al. [1987] J. Med. Chem. 30:481). Similar procedures obtain for the deoxy forms of the azanucleotides, deazanucleotides and are found in the same and additional sources (e.g., Robins et al. [1977] Can. J. Chem. 55:1251; DeClerq et al., supra). Protocols and procedures for synthesis of the 3'-azido, 3'amino, 2',3'-unsaturated, and 2',3'-dideoxy analogs are as reported (Lin et al. [1987] J. Med. Chem. 30:440; Serafinowski, P. [1987] Synthesis 10:879). Protection or derivatization of the 2'-OH with silyl or FRET moieties can be done as by Peterson and Anderson ([1989] *Silicon Compounds: Register and Review*, Petrarch Systems, Inc., pp. 60–70).

For enzymatic syntheses, mono- and triphosphate forms of the nucleoside analogs can be prepared by enzymatic phosphorylation with, e.g., polynucleotide kinase using established procedures, or by chemical phosphorylation. In general, the 5'-monophosphates are prepared chemically by the $POCl_2$ (Smith and Khorana [1958] J. Am. Chem. Soc. 80:1141; Yoshikawa et al. [1967] Tetrahedron Lett. 5095). The corresponding triphosphates can be chemically synthesized according to the same authors or Michelson ([1964] Biochim. Biophys. Acta 91:1); or Hoaro and Otts ([1965] J. Am. Chem. Soc. 87:1785). That is, the monophosphates are treated with carbodiimide (CDI) followed with tributylammonium pyrophosphate to give the triphosphorylated form. Where it is desired to phosphorylate analogs with exposed amino groups, such substituents can be thioacetylated by treatment with ethyl trifluorothioacetate according to the procedure of Thayer et al. ([1974] Biochem. J. 139:609).

B. Synthesis of Fluorescent Oligonucleotides

The present invention presents synthetic methods for the introduction of one or more of the fluorescent nucleoside analogs of the commonly occurring nucleotides into synthetic oligonucleotides.

1. Fluorescent phosphoramidites can be synthesized from the ribose and deoxy-ribose monomers of the fluorescent nucleoside analogs. According to the present invention, fluorescent residues are introduced into chemically synthesized oligonucleotides by first synthesizing the protected 3'-O-phosphoramidite of a nucleoside analog, e.g., 3'-deoxyformycin A; the phosphoramidite is then substituted for the corresponding standard phosphoramidite, in this case deoxy-adenosine-3'-O-phosphoramidite, and reacted with the oligonucleotide being synthesized on a solid support using standard phosphotriester chemical synthesis. The β-cyanoethyl derivatives may be selectively inserted at any desired position in a chemically synthesized oligonucleotide to produce oligomers of prescribed sequences of 60 or more bases in length and carrying any predetermined number of fluorescent bases.

For example, non-self-hybridizing oligonucleotides were synthesized which had the perfectly alternating sequences, $[AC]_x$ and $[FC]_x$, where x is the number of AC and FC dimer pairs and x had values of x=10, 15, 20, 25, 30, gave nearly identical values for both repetitive (>98%) and overall synthesis yields, and produced oligomers which differed only in that $[FC]_x$ was fluorescent, whereas $[AC]_x$ was not. Both olignomers hybridized specifically with complementary alternating oligomers of the sequence $[TG]_x$ but not with themselves or with noncomplementary sequences such as $[AG]_x$ and $[TC]_x$ as indicated by (i) ethidium bromide staining in agarose gels and (ii) the melting behavior of the hybrids. Equivalent values of the melt transition temperatures in 0.075M NaCl for the $[FC]_x:[TG]_x$ and $[AC]_x:[TG]_x$ hybrids varied by less than 1° C. for a given value of x (length of oligonucleotide). Specifically, one aspect of the present invention involves the synthesis of 3'-O-phosphoramidites of the fluorescent nucleotides and of their fluorescent structural analogs, the use of amidites to synthesize highly fluorescent oligonucleotides having prescribed sequences and the uses of such oligonucleotides as amplification primers, fluorescent oligonucleotide "tags," and hybridization probes.

Figure 10:
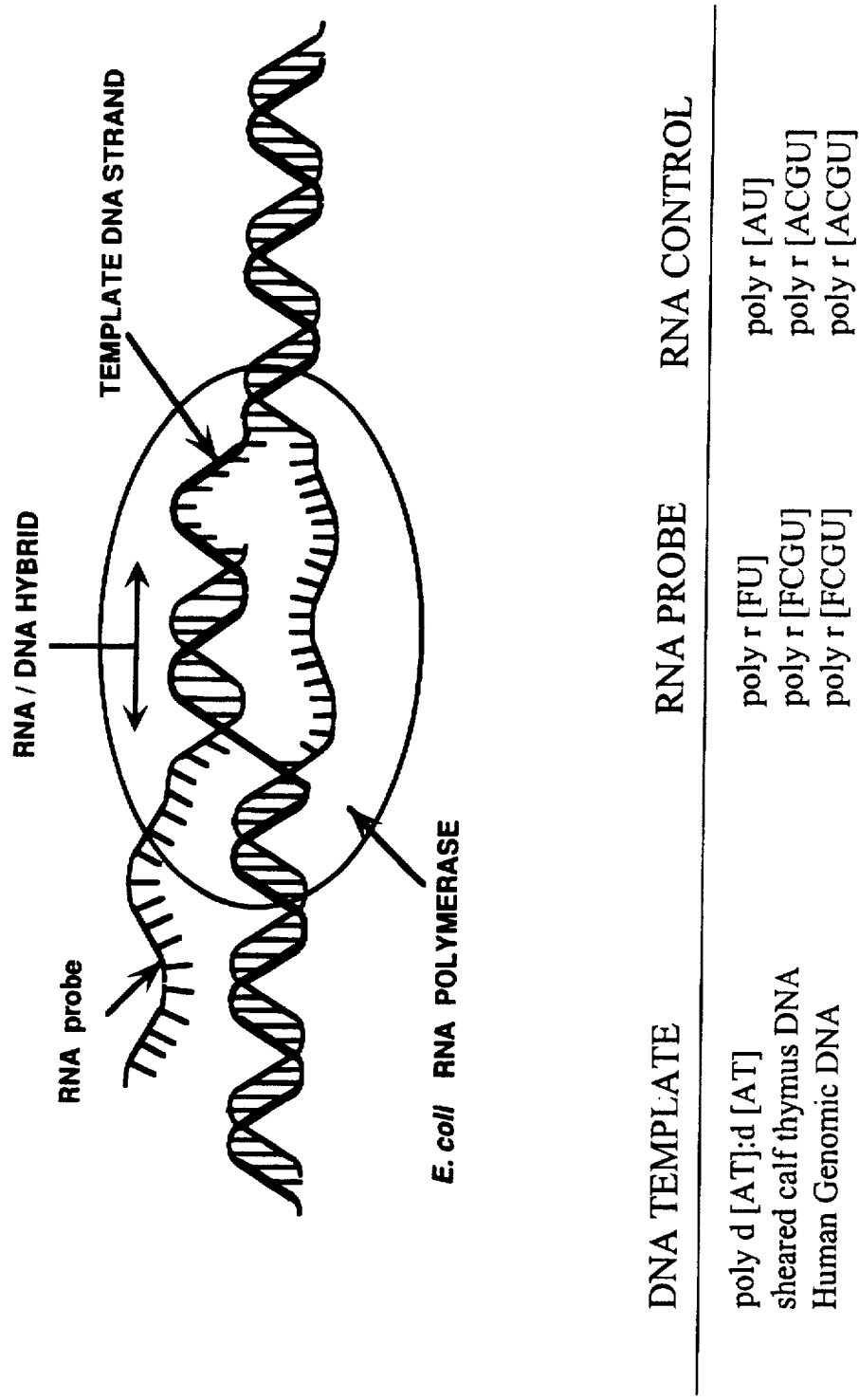
FIG. 10 is a diagram of RNA probe synthesis using FTP or STP.

2. Fluorescent polyribonucleotides and polydeoxyribonucleotides of prescribed sequences can be synthesized enzymatically using DNA templates from a variety of sources including those prepared by chemical synthesis, cloning techniques, or obtained from genomic DNA. Representative syntheses of RNA oligonucleotides using three such DNA templates, *E. coli* RNA polymerase, the rNTPs cytidine, uridine, and guanosine, together with the ribose triphosphate of either formycin A or adenosine, are illustrated in FIG. 10; the corresponding polydeoxyribonucleotides have been made by substituting 3' deoxyformycin-5'-triphosphate (FTP) for deoxy adenosine (DATP) in standard DNA polymerase syntheses and in DNA amplifications using thermostable DNA polymerase enzymes and the polymerase chain reaction (PCR). Comparable syntheses can be made by other substitutions, including, e.g., the fluorescent N-nucleosides, 2-amino purine, and 2,6-amino purine (also substituted for adenosine-5'-triphosphate) and the fluorescent C-nucleoside formycin B (substituted for guanosine-5'-triphosphate) in either their ribose and deoxyribose forms.

3. RNA and DNA can be enzymatically labeled by several methods including, but not limited to, (i) 5' DNA end-labeling using both the forward phosphorylation reaction (Richardson, C. C. [1965] PNAS 54:158) or the exchange kinase reaction (Van de Sande et al. [1973] Biochemistry 12:5050); (ii) mixed primer labeling by extending mixed sequence hexadeoxynucleotides annealed to restriction fragments (Feinberg, A, B. Vogelstein [1983] Anal. Biochem. 132:6; Feinberg, A., B. Vogelstein [1984] Anal. Biochem. 137:266); (iii) 3' DNA end-labeling using the enzyme, terminal deoxynucleotidyl transferase, to catalyze the repetitive addition (Okayama et al. [1987] Methods Enzymol. 154:3; Heidecker, G., J. Messing [1987] Methods Enzymol. 154:28) of mononucleotide units of the deoxytriphosphates, or single additions of deoxytriphosphates, of several of the fluorescent nucleoside analogs to the terminal 3'-hydroxyl of DNA initiators, including nonfluorescent probes of prescribed sequence, e.g., the *Chlamydia trachomatis* MOMP gene probe synthesized as described below; (iv) ligase labeling in which non-fluorescent "sticky-ended" or "nicked" RNA or DNA oligonucleotides are labeled by ligation with the appropriate fluorescent RNA or DNA oligomers (Pharmacia LKB [1989] Analects 17.2; Helfman, D. M. [1987] Methods Enzymol. 152:343); (v) nick translation, in which DNA polymerase is used to incorporate the triphosphates of the fluorescent analogs randomly in an existing DNA strand in a duplex (Meinkoth, J., G. M. Wahl [1987] Methods Enzymol. 152:91).

4. Hybridization, thermal melting, agarose gel characterization and fluorescence detection studies were used to characterize oligonucleotides of prescribed sequences. In some cases, the fluorescent oligonucleotides were complementary to known sequences of target DNA from clinically important pathogens or mutations, e.g., the MOMP gene sequence from *Chlamydia trachomatis*. In these studies, the templates used for enzymatic synthesis of the fluorescent oligonucleotides were the cloned fragments also intended for use later as the target DNA in subsequent hybridization studies. Hybridization of the oligonucleotides with target DNA results in quenching of the fluorescence of the structural analogs in a fluorescent probe, which fluorescence is recovered upon denaturation of the hybrid, thereby proving that hybridization has occurred. The self-hybridization of the synthetic oligonucleotide poly(rFrU), which is discussed at length, below, is representative of the results obtained in such experiments and is summarized in Table 1.

A preferred process according to the subject invention involves four basic steps. Initially the fluorescent structural analogs are chemically or biologically synthesized and, where appropriate, further derivatized as required to synthesize a fluorescent oligonucleotide probe. Second, a DNA or RNA probe molecule complementary to a nucleic acid sample of interest is constructed to have fluorescent nucleoside analogs which can be (i) distributed randomly or at specific locations throughout its length, or (ii) placed as terminal labels as described below. Third, the nucleic acid sample is then separated from unreacted monomers and can then be characterized directly, used as an extrinsic, non-specific label for tagging specific hybridization probes, or used directly as a hybridization probe. In the latter case, hybridization may take place on a solid phase to which either the target DNA/RNA or the fluorescent probe has been immobilized such as in Southern blot transfers, or "Dot-Blot" techniques, or it may occur in solution (herein, "solution hybridization"), after which probe/target hybrids are separated from unhybridized probes by simply washing or filtration. Finally, the fluorescence of the oligonucleotides hybridized to the target DNA/RNA is detected and quantified.

C. Construction of Fluorescent Probe Molecules

In accordance with the present invention, a preselected fluorescent nucleoside analog or mixture of fluorescent analogs is substituted specifically for one or more of the non-fluorescent commonly occurring nucleosides and is then incorporated into DNA or RNA oligonucleotides to create prescribed sequences. The prescribed sequences may be chosen to be equivalent in their Watson-Crick base pairing to a nucleotide sequence constructed from normally occurring nucleotides and complementary to a given target DNA or RNA sequence; such fluorescent probes are said to be analogous to the complementary sequence of the target DNA or RNA. The fluorescent probe may be synthesized by either enzymatic or chemical synthesis for subsequent applications such as (i) hybridization probes, (ii) amplimers for direct detection of amplifiable gene sequences complementary to a given set of primers, or (iii) as non-specific "universal" labels which can be attached to specific hybridization probes by, e.g., ligation.

Fluorescent nucleoside analogs of the commonly occurring ribo-, deoxy-, or dideoxyribonucleotides can be incorporated into nucleic acid polymers using one of several otherwise conventional enzymatic and chemical techniques including, but not limited to, those described here.

1. Enzymatic syntheses. Enzymatic syntheses include:

(a) The use of the enzyme DNase I to introduce small "nicks" into one strand of a double stranded DNA duplex. The holoenzyme form of *E. coli* DNA polymerase I can then be used to extend and repair these nicks using a mixture of fluorescent nucleotide analog triphosphates, e.g., deoxyformycin-5'-triphosphate (FTP), with commonly occurring deoxynucleotide triphosphates in the reaction mixture. This method introduces a large number of fluorophores randomly throughout the DNA polymer, including both strands of the double helix. In practice, the commonly occurring nucleotide, in this case dAdenosine-5'-triphosphate (dATP), can be eliminated entirely, and the dFTP substituted in its place, without significant loss of synthetic yield, loss of hybridization specificity, or strength of duplex formation as measured by the values of the DNA melting temperature.

(b) Alternatively, a variety of enzymes, including the Klenow fragment of DNA polymerase I and the T4 DNA polymerase, can be used to fill in overhanging single stranded regions of DNA produced by the prior actions of restriction enzymes. This method concentrates the fluorescent analogs at the end of each DNA strand. Similarly, fluorescent DNA oligonucleotides complementary to a specific DNA template can be synthesized (i) by using DNA fragments and *E. coli* DNA polymerase, or (ii) by constructing a recombinant plasmid containing the promoter for a specific DNA polymerase, e.g., T7 DNA polymerase, immediately 5'to the desired DNA sequence. The DNA polymerase will synthesize a complementary DNA molecule using ribonucleotides and analogs including, e.g., FTP as a substitute for ATP, present in the reaction mixture.

(c) A third incorporation method, which also produces a terminal concentration of fluorescent analogs, involves the use of the "tailing" enzyme, terminal deoxynucleotide transferase, to add a homopolymer or "tail" of fluorescent deoxy analogs to the 3' end of DNA oligomers. In practice, the yields obtained in the synthesis of homopolymers when substituting fluorescent analogs for the commonly occurring nucleosides is significantly less than the yield obtained in the synthesis of heteropolymers. Alternatively, a single fluorescent nucleoside analog may be added to the 3' OH of any oligomer using the same enzyme but the dideoxy form of a fluorescent analog or a 2'-protected fluorescent analog, including the FRET protected analogs, in exactly the same manner in which, e.g., dideoxy ATP (cordecypin), is used. A third alternative method of endlabeling hybridization probes utilizes the action of DNA ligase or RNA ligase, by which non-specific double or single stranded fluorescent oligonucleotides can be covalently coupled to either the 3' or 5' end of specific hybridization probes; the fluorescent oligonucleotides used in this fashion do not necessarily participate in the Watson-Crick base pairing which determines specificity of a probe, but may act solely as a generic or universal fluorescent "tag." With each of the foregoing methods, the DNA probes are double stranded and must be denatured to single stranded form using either heat or alkali treatment prior to their use for hybridization.

(d) A fourth incorporation method, which can also be used as a standard method of production of fluorescent probes having a prescribed length and sequence, uses the standard methods of DNA amplification and any of the several available DNA polymerases, including the thermostable DNA polymerases, e.g., Taq polymerase, useful in the polymerase chain reaction (PCR) method, but substitutes one of the fluorescent deoxyribonucleotide analogs, e.g., deoxyformycin-5-triphosphate or 5-amino-deoxyformycin B-5'-triphosphate for ATP and GTP, respectively, in the mix of nucleotide triphosphates. The fluorescent oligonucleotides are equivalent in yield and length to the non-fluorescent oligomer made with the commonly occurring nucleotides and hybridize to target (template DNA) with the same thermal stability and capacity to stain with ethidium bromide once the hybrid duplex has formed. In such amplifications, the production of fluorescent oligonucleotides can be taken directly as evidence of the presence of a particular sequence, or the identity can be further established by (i) hybridization with a defined complementary probe, and (ii) sequencing to establish the analogous sequence.

(e) Fluorescent RNA oligonucleotides complementary to a specific DNA template can be synthesized (i) by using DNA fragments and *E. coli* RNA polymerase, or (ii) by constructing a recombinant plasmid containing the promoter for a specific DNA dependent RNA polymerase immediately 5' to the desired DNA sequence, e.g., a DNA template bearing a T7 RNA polymerase promoter immediately 5' to the fragment of a cloned Chlamydia MOMP gene which is to be used as the target for hybridization with the probe. The corresponding DNA dependent RNA polymerase will synthesize an analogous complementary RNA molecule using ribonucleotides, including, e.g., FTP as a substitute for ATP and UTP instead of TTP, present in the reaction mixture. The resulting single stranded probes can be used directly in a subsequent hybridization reaction without a denaturing step.

2. Chemical syntheses. The protected fluorescent deoxynucleoside analog-3'-O-phosphoramidites, typically those in which $R_5$=dimethoxytrityl, $R_{15}$=isopropyl, and $R_{10}$=methyl or beta-cyanoethyl, are coupled to the 5'-OH of a growing oligonucleotide attached to a solid support using standard phosphoramidite DNA synthesis techniques (Cf Atkinson, T., M. Smith [1984] In *Oligonucleotide Synthesis: A Practical Approach*, M. J. Gait, ed., IRL Press, Oxford, pp. 35–82). Solid support-bound oligonucleotide, which has already been acid washed to deprotect the 5'-OH group, is reacted with 5'-trityl protected deoxynucleoside analog-3'-O-phosphoramidite in anhydrous acetonitrile in the presence of tetrazole under argon, washing away excess reagents, and then oxidizing the phosphite product to the desired phosphate with a solution of iodine in aqueous THF, and washing with anhydrous acetonitrile. After acid washing to deprotect the new 5' terminus, the cycle can be repeated as many times as necessary to achieve the desired length and sequence; additional nucleotides which are added may be the commonly occurring nucleotides or they may be additional fluorescent nucleoside analogs. Accordingly, one or more fluorophores may be incorporated within a given probe up to and including complete substitution of, e.g., all of the A residues in a desired sequence with formycin residues. The couplings can be performed manually in a minireactor vial utilizing a 10 minute coupling time, or on a Pharmacia LKB Gene Assembler or similar instrument utilizing the programmed synthesis protocols. The fluorescent oligonucleotide is then isolated by cleaving the DNA from the porous glass support by incubation at 55° C. overnight in NH$_4$OH:ethanol (3:1). The fluorescent DNA containing ammonium hydroxide solution can then be quickly dried in a Speed-Vac and then separated from failure sequences of a QEAE-HPLC column using a shallow salt and pH gradient. Yields for the nucleoside analog phosphoramidites are comparable to those obtained with standard amidites based on repetitive yield calculated from trityl cation release at the deprotection step.

To provide specific illustrations of how to construct and use probe molecules containing a fluorescent nucleoside analog, following are examples which illustrate procedures, including the best mode, for practicing the invention. These examples should not be construed as limiting. All percentages are by weight and all solvent mixture proportions are by volume unless otherwise noted.

EXAMPLE 1

Complete Enzymatic Substitution of FTP for ATP in RNA Probes

RNA oligonucleotides were synthesized from three DNA templates (FIG. 10) using (i) FTP as a substitute for ATP, and (ii) a purified *E. coli* RNA polymerase as originally described by Ward et al. ([1969] J. Biol. Chem. 12:3242), except that synthesis was allowed to run for three hours at 37° C. before the reaction was stopped; FTP effectively replaced ATP but not any of the other three normal nucleotides CTP, UTP, or GTP.

At the end of the synthesis, reaction products were separated from unreacted reagents by separation at 4° C. on Sephadex G-50 in normal saline at pH 7.

In the reaction, FTP is an effective substrate for RNA polymerase with both native and denatured DNA as well as with synthetic deoxynucleotide polymer templates. In samples containing CTP, UTP, GTP, RNA polymerase, one of the DNA templates, and either FTP or ATP, a high molecular weight product eluted from either sample in the void volume while the amount of monomeric NTP in the retained fraction from either sample was correspondingly reduced by >70%. No high molecular weight fraction other than the small amount of template eluted from enzyme-free controls and unreacted rNTPs were undiminished; similarly, template-free controls contained only unreacted rNTPs which co-eluted in the retained volume with standard ribonucleotide triphosphates. Similar results were obtained with a variety of DNA templates from natural and synthetic sources, including the alternating copolymers poly d(AC), poly (AG), and poly (ACGT). Moreover, comparable yields of high molecular weight oligomer were obtained from syntheses in which (i) the N-nucleoside analogs 2,6-diamino-adenosine-5'-triphosphate or 2-diamino-adenosine-5'-triphosphate were substituted for ATP in the reaction mix, or (ii) the C-nucleosides formycin B-5'-triphosphate ($F_bTP$) or -amino-formycin B-5'-triphosphate ($aF_bTP$) were substituted for GTP in the reaction mix and using poly (TG) or poly (GC) as the DNA template. No matter what the template, yields obtained by substituting several of the deaza- and aza-nucleoside analogs for ATP or GTP were dramatically lower.

EXAMPLE 2

The Fluorescence of Nucleoside Analog RNA Probes and Proof of Their Hybridization in Solution The effective utilization of FTP in the poly d(AT) directed synthesis in Example 1 produced a polymer approximately 300–500 bases in length which, when hydrolyzed and/or sequenced, proved to be a perfectly alternating replicate of the DNA template, but with the sequence: poly (FU). As predicted from this sequence, the product could be annealed to like chains by a single thermal cycle, thereby creating the putative product poly (FU):poly (FU); unlike the comparably treated poly (FC), which showed no evidence of self-hybridization as expected, the annealed hybrids of poly (FU):poly (FU) stained with ethidium bromide in agarose gels and gave a sharp thermal transition in both absorbance and fluorescence, proving that the probes could hybridize both effectively and specifically. The absorbance and emission spectra of the purified poly (FU), poly (FC), poly (FG), poly ($UF_b$), poly ($CaF_b$), and poly (FCGU) differ from those of purified poly (AU), poly (AC), poly (AG), poly (TG), and poly (ACGT) controls in four respects: (i) the far UV absorbance maximum is shifted slightly for the analog-containing products, to 265 nm as compared to 260 nm for the controls; (ii) there is a significant, highly structured absorbance (3 peaks at room temperature) between 290 nm and 330 nm with negligible absorbance at 340 nm; (iii) an excitation maximum appears at 312 nm; and (iv) there is a broad emission band extending into the visible wavelengths with a peak at 405 nm (Stokes shift=93 nm). It is an important property that the fluorescence is fully quenched in, e.g., the poly (FU):poly (FU) hybrid, and cannot be detected until the strands are denatured by raising the pH of the solution to values >pH 10. Once denatured, the fluorescence of the oligomer is fully integratable, with relative fluorescence intensity >40% of peak intensity over the range 360 nm to 460 nm.

TABLE 1

Properties of hybrid formation by poly (AU) and poly (FU)

| RNA:RNA HYBRID | DENATURED HYBRID WAVELENGTH MAXIMA | | | INTACT HYBRID | | |
| --- | --- | --- | --- | --- | --- | --- |
| | ABSORBANCE | EXCITATION | EMISSION | LENGTH (BASE PAIRS) | ETHIDIUM BROMIDE STAINING | MELT TEMP. |
| r[AU]:r[AU] | 260 nm | — | — | 150–300 | yes | 32° C. |
| r[FU]:r[FU] | 266 nm | 312 nm | 405 nm | 150–300 | yes | 33° C. |

EXAMPLE 3

Hybridization of Fluorescent Probes to Target RNAs and Target DNAs: Uses of Linkers to Allow Solid Phase Detection The synthetic template poly (TG) was used to produce the complementary RNA probes poly (AC) and poly (FC), neither of which is self complementary and in which hybrids could not be annealed or detected; of the two only the poly (FC) was fluorescent. In a parallel experiment, a poly (AC) template was amplified using the biotinylated synthetic 22-mer primers, $5'BIOTIN-(TG)_{11}3'$, together with standard polymerase chain reaction (PCR) methods to produce the DNA amplimers having the sequence, $5'BIOTIN-poly (TG)3'$, then separated from the unreacted primers by gel sizing and/or QEAE ion exchange chromatography, after which the polymers were radioactively labeled using $^{32}P$-ATP and the enzyme polynucleotide kinase. When mixed separately, but in equimolar amounts, with the biotinylated amplimers, $5'BIOTIN-poly (TG)3'$, both of the RNA probes, poly (AC) and poly (FC), formed hybrids which could be characterized by (i) ethidium bromide staining, and (ii) melting behavior; as expected, the fluorescence of the poly (FC) probe was quenched by hybridization. The hybrids could then be adsorbed via the $5'BIOTIN$ moiety to avidinylated beads, washed to remove unhybridized poly (FC), and equal aliquots assayed for radioactivity and fluorescence. Prior to denaturation of the washed sample, detectable fluorescence in the solution was negligible; when denatured in high pH buffer, the amount of poly (FC) which had been hybridized, when estimated from the fluorescence of standardized dilutions of the probe, was within 1% of the amount of the target DNA, $5'BIOTIN-poly (TG)3'$, as measured by the amount of radioactive label in the sample as compared to standardized dilutions.

EXAMPLE 4

Hybridization of Fluorescent Probes Synthesized from Nucleoside Analog-3'-O-Phosphoramidites to Target DNAs In a validation of the use of the phosphoramidites of the fluorescent nucleoside analogs, n-mers which varied in length in multiples of 5 bases from 25-mers to 60-mers, and having the sequence (AC), or (FC)X, where x=12.5, 15, 17.5, 20, 22.5, 25, 27.5, or 30, were synthesized in parallel using either dAdenosine-3'-O-phosphoramidite or dF-3'-O-phosphoramidite together with dC-3'-O-phosphoramidite in a Pharmacia LKB Gene Assembler. After cleavage from the solid phase and purification of QEAE-Sepharose, the fluorescent oligomers $(FC)_x$ of defined length could be hybridized to the radiolabeled amplimers of poly (TG), from Examples 2 and 3, above, as assessed by DNA melting behavior, ethidium bromide staining, and the reappearance if quenched fluorescence following denaturation of the hybrid.

EXAMPLE 5

Assay for *Chlamydia trachomatis* Using an FTT Substituted RNA Probe

Figure 11:
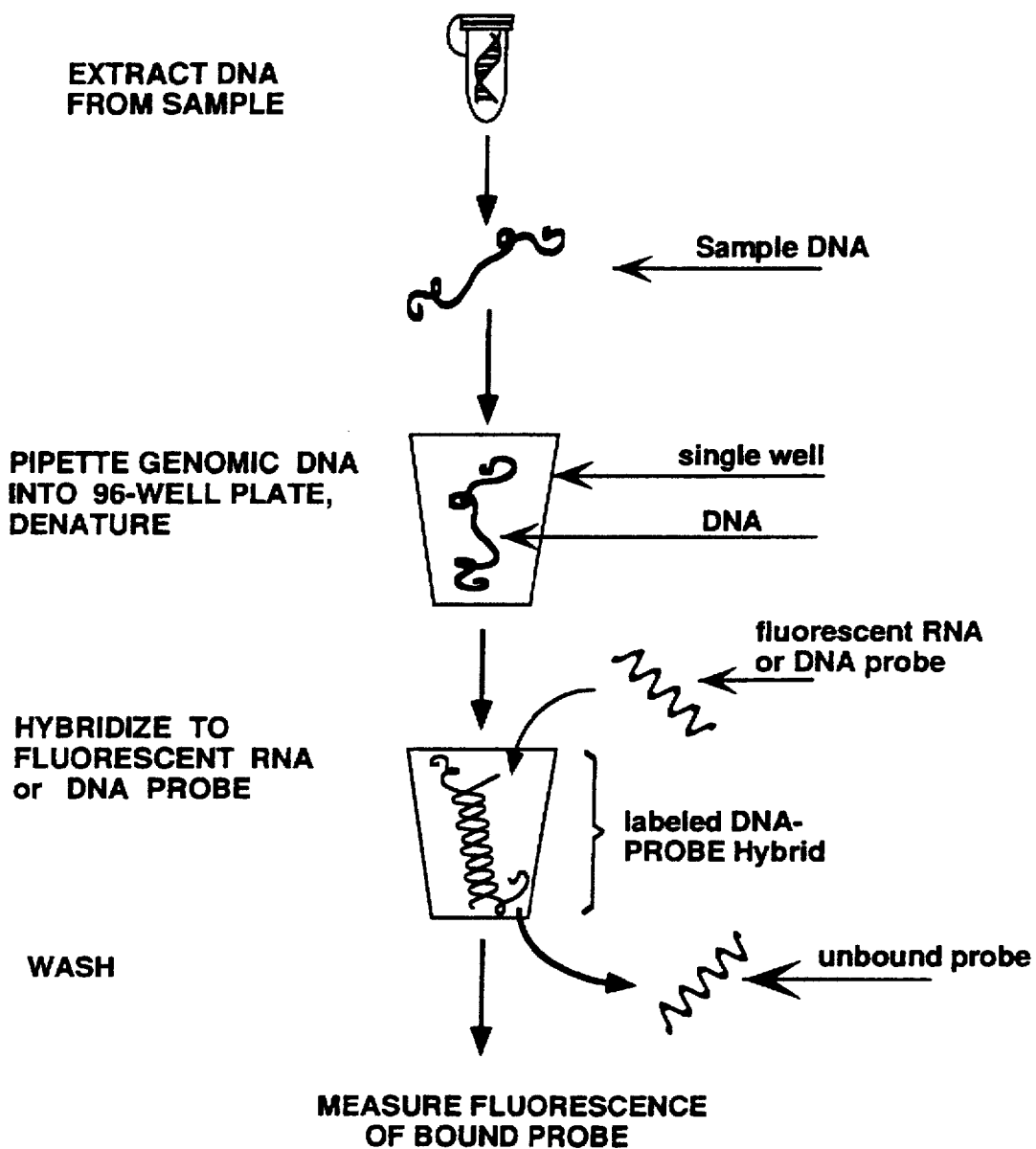
FIG. 11 is a diagram of detection of a target DNA sequence in genomic DNA by solution hybridization with fluorescent probes.
Figure 12:
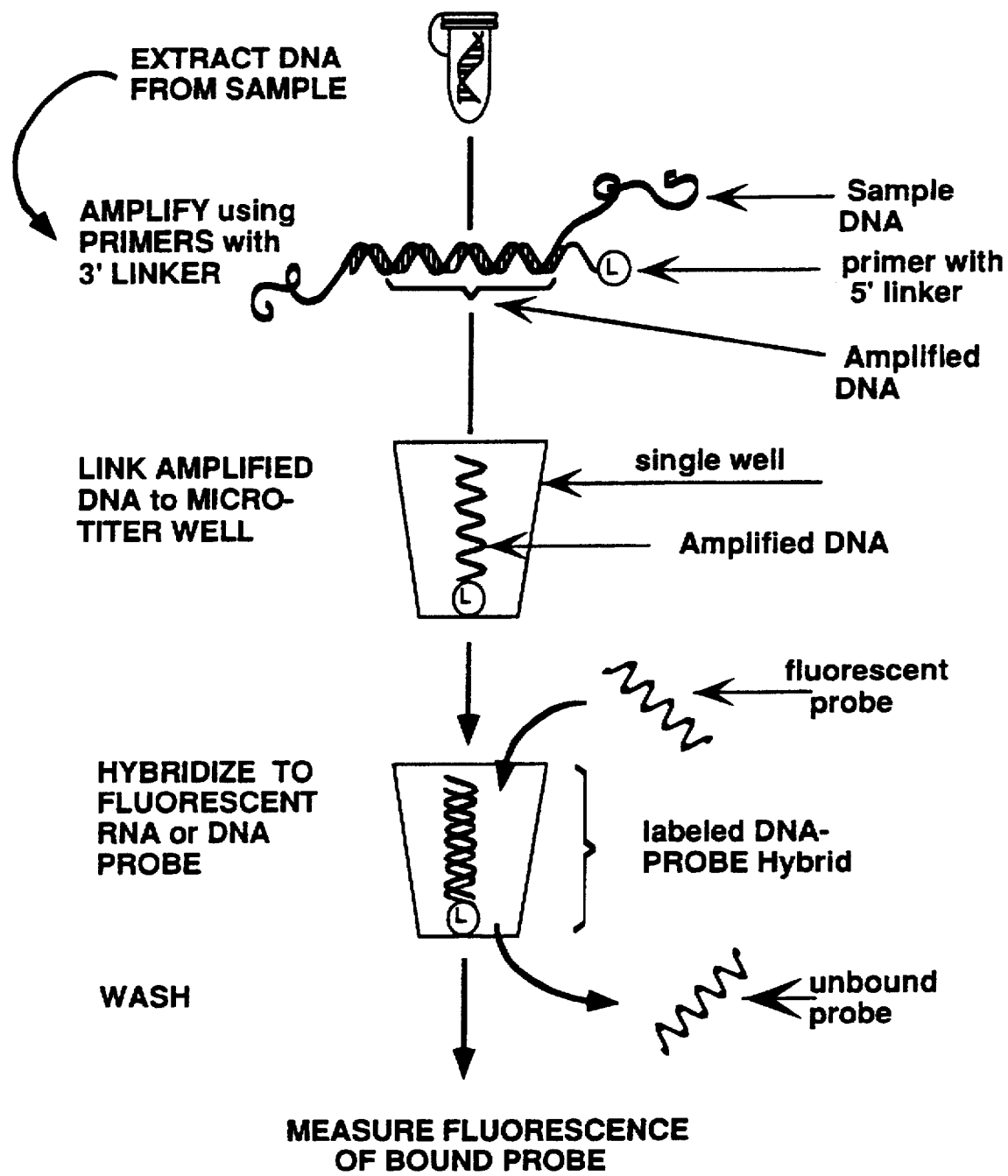
FIG. 12 is a diagram of detection of an amplified DNA segment by solution hybridization with fluorescent probe.

*Chlamydia trachomatis* is an obligatory intracellular pathogen which, in its active infectious stages, contains from $3\times10^3$ to $4\times10^3$ copies of ribosomal RNA (rRNA) and one copy of genomic DNA/bacterium. A primer pair, one of which contained a 5'-biotinylated T7 promoter which was 5' to the hybridizing primer sequence, was used to amplify a 150 base pair DNA segment of the MOMP gene from a stock strain of *C. trachomatis* L2. Approximately 500 ng of the DNA fragment, which contained the T7 RNA polymerase promoter at the 5' end, was transcribed with T7 RNA polymerase in the presence of rCFP, rUTP, rGTP, and with either rFTP or rATT (+control). The reaction was stopped by heat inactivating the enzyme for 3 minutes at 100° C. Unincorporated rNTPs were separated from the labeled RNA by gel sizing chromatography on a Sephadex G-25 column, after which the probe concentration was estimated from its absorbance at 260 nm. Using a simple dual monochromator fluorescence spectrophotometer, $10^{-14}$ moles of the RNA probe could be easily detected using (i) excitation at 312 nm and a 10 nm excitation slit width, and (ii) peak height detection at 405 nm with a 10 nm emission slit width. A fluorimeter designed for increased sensitivity (i) high intensity excitation from 300 nm to 325 nm, (ii) replaced the monochromators with a single high transmittance cutoff filter at the photodetector, (iii) used a peltier device-cooled, high sensitivity photodetector, (iv) full integration of fluorescence emission from 360 nm to 460 nm, and (v) time resolved fluorescence integration, to achieve probe detection sensitivities of from $10^{-17}$ to $10^{-18}$ moles of the RNA probe, equivalent to the amount of RNA expected from between 1,000 and 10,000 of the bacteria. Two hundred microliters of either (i) *C. trachomatis* genomic DNA, or (ii) the amplified target DNA were mixed with 200 µL of a 1/200 dilution of the probe in hybridization buffer (0.15M NaCl, 0.02M sodium citrate, 0.02M HEPES, 0.004M EDTA, pH 7.4) and the mixture boiled for 3 minutes, after which they were allowed to cool slowly to room temperature over one hour. An aliquot of the genomic DNA sample was eluted into an ultrafiltration microtube or 96-well filter plate (pore size=0.1 µm) as illustrated in FIG. 11, washed 5 times with 0.15M NaCl, 0.02M sodium citrate, pH 7.4, after which the sample was divided in two, one half denatured in high pH buffer, and both aliquots scanned to measure fluorescence background and the fluorescence of hybridized probe, respectively. Target DNA amplimers were treated similarly except that the 5'-biotinylated primer end of the target DNA segments were first adsorbed to avidinylated magnetic beads (2.8 µm diameter) so that the sample could be washed without loss of material (FIG. 12). With either treatment, fluorescence of the probe may be detected at dilutions of the sample which contain less than $10^{-17}$ moles of target DNA, roughly equivalent to the sensitivity required to detect from 100 to 10,000 bacteria if a single probe were used to detect rRNA from infectious Chlamydia. The probe used here is 150 bases in length, contains approximately 38 formycin residues per probe, and binds only to a single segment of the target nucleotide as illustrated in the upper half of the figure, below. Since the rRNA of Chlamydia is typically between 3000 and 5000 bases in length, and the genome $>10^6$ bases in length, sensitivity may be increased significantly by use of a probe "cocktail" made of as many as 5 or 10 different probe sequences, each of which can bind to discrete segments of the target rRNA or target DNA.

EXAMPLE 6

The Use of Non-Specific and Non-Hybridizing Fluorescent Oligomers as Universal Fluorescent "Tags" by Ligation or Chemical Linkage Simple modification of the template to produce a "sticky end" at the 3', 5', or both 3' and 5' termini, e.g., to $5'ACGT-polyd(AT)$, $polyd(AT)-TGCA3'$, or $5'ACGT-polyd(AT)-TGCA3'$, respectively, enabled synthesis of RNA probes with all of the above properties, but which could also be ligated, either (i) to like strands to produce longer fluorescent probes, or (ii) to other hybridization sequences specific for a prescribed target DNA. The latter is a particularly useful way in which to produce a universal label for any cloned DNA fragment, and allows a given probe to be identified by two non-hybridizing but highly fluorescent sequences at its termini, without the need to denature the hybrid for detection as was seen with the simple poly (FU) probe, above. Equivalent non-hybridizing universal probes can be readily made by chemical synthesis using, e.g., the etheno analog phosphoramidites, e.g., 1.$N_6$-ethenoAdenosine-3'-O-phosphoramidite (eA), to synthesize non-specific tags which can subsequently be linked to any hybridization probe. In general, the 3' or 5' termini of such universal probes can also be prepared for chemical rather than enzymatic attachment to other oligomers or solid phases, through the addition of, e.g., 5'-amino hexyl, 5'-sulfiydryl hexyl, 3'-aminohexyl amino, N-hydroxysuccinimide esters, and other such linkers.

EXAMPLE 7

Attachment of 5' and 3' Linkers for Immobilization of the Oligonucleotides and Hybrids or for Attachment of Fluorescent Oligomers as "Labels"

The chemistries and procedures of the invention can be used to create and characterize any probe synthesized using fluorescent nucleoside analogs, whether the synthesis is enzymatic or chemical, for both fluorescence and hybridization specificity. Such probes can be used not only in the solution hybridization formats described here, but also in the more frequently used laboratory procedures such as "dot-blot" detection, electrophoresis in agarose or polyacrylamide gels, Southern blotting, and hybridization on filters and membranes, as well as separation of the hybrids by HPLC or capillary electrophoresis methods. Although linkers are not essential to the solution hybridization, any appropriate affinity linker such as biotin/avidin or homo- or heterobifunctional linker can be used to capture the probe or hybrid for purposes of concentration, isolation, or detection, as illustrated for the PCR amplified DNA fragments of FIG. 12. The present invention includes linker derivatized fluorescent nucleotides, as well as oligonucleotides, linker derivatized primers for use in amplification and subsequent detection with fluorescent oligonucleotide probes, oligonucleotide probes, plasmids, and therapeutics made or otherwise "tagged" therefrom, and/or their uses and applications such as are described herein. Such derivatizations include, but are not limited to, transaminations to purine or pyrimidine nucleosides and/or their fluorescent structural analogs, amino-thiol, azido-, aldehyde, hydroxysuccinimide, 5' aminoalkyl-3'-O-phosphoramidite, 5'-thioalkyl-3'-O-phosphoramidite, 3'-aminohexyl amino, amino silanes, and aminosilyl derivatives and other such linkers and groups reactive with linkers or in condensation reactions such as Schiff base condensations of 3' or 5' oxidized cis-diols, as are familiar to one skilled in the art. To illustrate this a specific case is offered:

(i) a set of non-fluorescent amplification primers for the MOMP gene sequence was chemically synthesized; at the end of synthesis an additional cycle was used to add 5'-aminohexyl-3'-O-phosphoramidite to the 5' terminus of the completed primer with the addition chemically synthesized, using standard phosphotriester chemistry.

(ii) Following cleavage from the solid phase support in strong ethanolic base, the terminal amino group of each strand was reacted with NHS-biotin ester to provide the 5' biotinylated primers.

(iii) The primers were used for standard amplification, after which the amplimers were captured on avidinylated 96-well filter plates and washed to remove unreacted materials and contaminants.

(iv) The captured amplimers were hybridized with fluorescent analog labeled oligonucleotide probes as described above and the amount of target sequence in the amplimers quantified.

Included in the present invention are such attachments of fluorescent oligonucleotides to other fluorescent or non-fluorescent oligonucleotides to immobilizing beads, filters, or activated plastic plates and done through enzymatic attachment such as ligation, or chemical attachment through such linkers as are described herein.

EXAMPLE 8

Uses of Fluorescence Resonance Energy Transfer (FRET) to Broaden or Enhance the Uses of Fluorescent Nucleoside Analogs and Probes Oligonucleotides can be synthesized or derivatized as derived herein which have two or more spectrally distinct, detectable labels, either by using two or more nucleoside analogs with discrete fluorescence emission characteristics, or by use of a covalently attached FRET acceptor, such as is described above. FRET acceptors can also be used to enhance or broaden the sensitivity of the detection for the fluorescent probes, if they are simply available in solution to act as acceptors of the probe emission. For example, the excitation spectra of such dyes as the coumarins, e.g., 7-amino-4-methylcoumarin-3-acetate, 7-methylumbelliferone, the naphthalene and anthracene dyes, etc., overlap the emission spectrum of oligomers constructed from the fluorescent nucleoside analogs, e.g., poly (FU), but not the oligomers' excitation spectrum. Such dyes as 7-amino-4-methylcoumarin-3-acetate may thus be used either (i) as a covalently attached FRET acceptor, e.g., by reacting the N-hydroxysuccinimide ester with prescribed amino groups on the oligomer, or (ii) by simply adding the dye to a solution of the probe to act as a FRET indicator of probe fluorescence. In addition to the obvious advantages of providing a second fluorescent label to the hybridization probe, this methodology allows amplification of the probe signal through more efficient capture of the emitted light, reduction of background light due to light scattering from excitation sources, and detection at longer visible wavelengths.

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. A hybridization complex consisting of a polynucleotide molecule hybridized to a target nucleotide sequence:

wherein said polynucleotide molecule consists essentially of nucleotides joined through phosphodiester bonds wherein said polynucleotide molecule comprises a series of nucleotides which are hybridized to a target nucleotide sequence through the formation of hydrogen bonds between said series of nucleotides and said target nucleotide sequence; and wherein the nucleotides of said polynucleotide molecule are arranged in an order such that (a) a single molecule of said isolated polynucleotide molecule will not form enough hydrogen bonds with itself to cause self-annealing at standard room temperature; and (b) a single molecule of said isolated polynucleotide molecule will not form enough hydrogen bonds with other identical molecules of said isolated polynucleotide molecule to cause hybridization to occur;

and wherein said isolated polynucleotide molecule comprises at least one fluorescent nucleotide which can be detected by its emission of fluorescence at standard room temperature.

2. The hybridization complex, according to claim 1, wherein said fluorescent nucleotide is a deoxyribonucleotide or dideoxyribonucleotide.

3. The hybridization complex, according to claim 1, wherein said fluorescent nucleotide specifically base-pairs with a complementary base of said target nucleotide sequence.

4. A hybridization complex consisting of a polynucleotide molecule hybridized to a target nucleotide sequence:

wherein said polynucleotide molecule consists essentially of nucleotides which are hybridized to a target nucleotide sequence wherein the nucleotides of said polynucleotide molecule are arranged in an order such that a single molecule of said polynucleotide molecule will not self-hybridize at standard room temperature; and wherein said polynucleotide molecule comprises at least one fluorescent nucleotide which can be detected by its emission of fluorescence at standard room temperature.

5. The hybridization complex, according to claim 4, wherein said fluorescent nucleotide specifically base-pairs with a complementary base of said target nucleotide sequence.

6. The hybridization complex, according to claim 4, which has no label for detection other than said fluorescent nucleotide.

7. A hybridization complex consisting of a polynucleotide molecule hybridized to a target polynucleotide:

wherein said polynucleotide molecule has the following characteristics:

(a) the polynucleotide molecule will specifically hybridize with the target polynucleotide under assay conditions:

(b) the polynucleotide molecule will not self-hybridize under assay conditions;

(c) the polynucleotide molecule has no non-nucleotide detectable label; and (d) the polynucleotide molecule comprises at least one fluorescent nucleotide which can be detected by its emission of fluorescence at standard room temperature.

* * * * *

UNITED STATES PATENT AND TRADEMARK OFFICE
CERTIFICATE OF CORRECTION

Page 1 of 2

PATENT NO. : 5,763,167

DATED : June 9, 1998

INVENTOR(S) : Michael J. Conrad

It is certified that error appears in the above-identified patent and that said Letters Patent is hereby corrected as shown below:

Column 1, line 27: "$R_g$ is H" should read --$R_9$ is H--;

line 43: "(NH, SH, " should read --($NH_2$, SH, --; and lines 53-54: "or $R_1$-$R_2$- ($CH_2$)-$R_3$- " should read --or $R_1$-$R_2$-$(CH_2)_x$ -$R_3$- --.

Column 2, line 30: "-chemical" should read chemical--.

Column 3, line 39 "Jablonsid" should read --Jablonski--.

Column 9, line 49: "benmimidazole" should read --benzimidazole--.

Column 11, line 21: "CTT GOT TCG" should read --CTT GGT TCG--; and line 57: "nbonucleoside" should read --ribonucleoside--.

Column 21, line 45: "(AC). or (FC)X" should read --$(AC)_x$ or $(FC)_x$,--.

UNITED STATES PATENT AND TRADEMARK OFFICE
CERTIFICATE OF CORRECTION

PATENT NO. : 5,763,167

DATED : June 9, 1998

INVENTOR(S) : Michael J. Conrad

It is certified that error appears in the above-identified patent and that said Letters Patent is hereby corrected as shown below:

Column 22, line 5: "rCFP" should read --rCTP--; and line 6: "rATT" should read --rATP--.

Column 23, line 19: "sulfiydryl" should read --sulfhydryl--.

Signed and Sealed this

Second Day of March, 1999

*Attest:*

Q. TODD DICKINSON

*Attesting Officer*     *Acting Commissioner of Patents and Trademarks*